(12) United States Patent
Barthe et al.

(10) Patent No.: US 9,566,454 B2
(45) Date of Patent: Feb. 14, 2017

(54) METHOD AND SYSEM FOR NON-ABLATIVE ACNE TREATMENT AND PREVENTION

(75) Inventors: Peter G. Barthe, Phoenix, AZ (US); Michael H. Slayton, Tempe, AZ (US); Inder Raj S. Makin, Mesa, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 1466 days.

(21) Appl. No.: 11/738,682

(22) Filed: Apr. 23, 2007

(65) Prior Publication Data

US 2008/0294073 A1 Nov. 27, 2008

Related U.S. Application Data

(60) Provisional application No. 60/826,039, filed on Sep. 18, 2006.

(51) Int. Cl.
*A61N 7/02* (2006.01)
*A61B 17/00* (2006.01)
(Continued)

(52) U.S. Cl.
CPC ............... *A61N 7/02* (2013.01); *A61B 8/4272* (2013.01); *A61B 2017/00747* (2013.01); *A61B 2017/22008* (2013.01); *A61B 2018/00666* (2013.01); *A61M 37/0092* (2013.01); *A61N 7/00* (2013.01); *A61N 2007/0008* (2013.01); *A61N 2007/0078* (2013.01)

(58) Field of Classification Search
CPC .... A61N 7/02; A61N 7/00; A61N 2007/0008; A61N 2007/0078; A61B 2017/00747; A61B 2017/22008; A61B 2018/00666; A61B 8/4272; A61M 37/0092

USPC ..... 600/439, 438; 604/20–22; 606/27, 9, 32, 606/13, 22; 601/2–4
See application file for complete search history.

(56) References Cited

U.S. PATENT DOCUMENTS 2,427,348 A 9/1947 Bond et al.
3,913,386 A 10/1975 Saglio
(Continued)

FOREIGN PATENT DOCUMENTS

CA 2580720 3/2006
CA 258341 4/2006
(Continued)

OTHER PUBLICATIONS

International Preliminary Report on Patentability for International Application No. PCT/US2007/078712 dated Dec. 16, 2008.
(Continued)

*Primary Examiner* — Bo J Peng
(74) *Attorney, Agent, or Firm* — Quarles & Brady, LLP

(57) ABSTRACT

A method and system for non-ablative acne treatment and prevention is disclosed. The method utilizes ultrasound energy which is targeted at a region of interest to treat existing acne and prevent future acne from forming. The application of ultrasound energy causes numerous physiological effects that treat acne. Some of these physiological effects comprise reducing sebum, increasing perfusion at the region of interest, denaturing proteins at the region of interest, creating an uninhabitable environment at the region of interest, initiating programmed cell death at the region of interest and the initiation of mechanical effects at the region of interest.

20 Claims, 14 Drawing Sheets

(51) Int. Cl.
  *A61B 17/22* (2006.01)
  *A61B 18/00* (2006.01)
  *A61N 7/00* (2006.01)
  *A61B 8/00* (2006.01)
  *A61M 37/00* (2006.01)

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh et al. |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,973,096 A | 11/1990 | Jaworski |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,190,518 A | 3/1993 | Takasu |
| 5,190,766 A | 3/1993 | Ishihara |
| 5,191,880 A | 3/1993 | McLeod et al. |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlaeger et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger et al. |
| 5,371,483 A | 12/1994 | Bhardwaj |
| 5,375,602 A | 12/1994 | Lancee et al. |
| 5,380,280 A | 1/1995 | Peterson |
| 5,380,519 A | 1/1995 | Schneider et al. |
| 5,391,140 A | 2/1995 | Schaetzle |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams, Jr. et al. |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,458,596 A | 10/1995 | Lax et al. |
| 5,460,179 A | 10/1995 | Okunuki et al. |
| 5,460,595 A | 10/1995 | Hall et al. |
| 5,469,854 A | 11/1995 | Unger et al. |
| 5,471,988 A | 12/1995 | Fujio et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |

(56) References Cited

U.S. PATENT DOCUMENTS

| | | |
|---|---|---|
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz et al. |
| 5,529,070 A | 6/1996 | Augustine et al. |
| 5,540,235 A | 7/1996 | Wilson |
| 5,558,092 A | 9/1996 | Unger et al. |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton et al. |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,871,524 A | 2/1999 | Knowlton |
| 5,873,902 A | 2/1999 | Sanghvi |
| 5,876,431 A | 3/1999 | Spehr et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fulmer |
| 5,971,949 A | 10/1999 | Levin |
| 5,977,538 A | 11/1999 | Unger et al. |
| 5,984,882 A | 11/1999 | Rosenschein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,036,646 A | 3/2000 | Barthe et al. |
| 6,039,048 A | 3/2000 | Silberg |
| 6,042,556 A | 3/2000 | Beach et al. |
| 6,049,159 A | 4/2000 | Barthe et al. |
| 6,050,943 A | 4/2000 | Slayton et al. |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein |
| 6,113,559 A | 9/2000 | Klopotek |
| 6,120,452 A | 9/2000 | Barthe et al. |
| 6,123,081 A | 9/2000 | Durette |
| 6,126,619 A | 10/2000 | Peterson et al. |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias et al. |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe et al. |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |

(56) References Cited

U.S. PATENT DOCUMENTS

| | | |
|---|---|---|
| 6,246,898 B1 | 6/2001 | Vesely et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 * | 7/2002 | Cain et al. .................. 600/439 |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas et al. |
| 6,430,446 B1 | 8/2002 | Knowlton |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton et al. |
| 6,440,121 B1 | 8/2002 | Weber |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe |
| 6,500,121 B1 | 12/2002 | Slayton et al. |
| 6,500,141 B1 | 12/2002 | Irion |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,540,679 B2 | 4/2003 | Slayton et al. |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,572,552 B2 | 6/2003 | Fukukita |
| 6,575,956 B1 | 6/2003 | Brisken et al. |
| 6,595,934 B1 | 7/2003 | Hissong et al. |
| 6,599,256 B1 | 7/2003 | Acker |
| 6,607,498 B2 | 8/2003 | Eshel |
| 6,618,620 B1 | 9/2003 | Freundlich et al. |
| 6,623,430 B1 | 9/2003 | Slayton et al. |
| 6,626,854 B2 | 9/2003 | Friedman |
| 6,626,855 B1 | 9/2003 | Weng et al. |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin |
| 6,669,638 B1 * | 12/2003 | Miller et al. .................. 600/438 |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laugharn, Jr. et al. |
| 6,719,694 B2 | 4/2004 | Weng |
| 6,726,627 B1 | 4/2004 | Lizzi et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton et al. |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton et al. |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco et al. |
| 7,303,555 B2 | 12/2007 | Makin et al. |
| 7,331,951 B2 | 2/2008 | Eshel et al. |
| 7,347,855 B2 | 3/2008 | Eshel |
| RE40,403 E | 6/2008 | Cho et al. |
| 7,393,325 B2 | 7/2008 | Barthe et al. |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton et al. |
| 7,530,958 B2 | 5/2009 | Slayton et al. |
| 7,571,336 B2 | 8/2009 | Barthe et al. |
| 7,601,120 B2 | 10/2009 | Moilanen et al. |
| 7,615,015 B2 | 11/2009 | Coleman |
| 7,615,016 B2 | 11/2009 | Barthe et al. |
| 7,686,763 B2 | 3/2010 | Vaezy et al. |

(56) References Cited

U.S. PATENT DOCUMENTS

| | | |
|---|---|---|
| 7,695,437 B2 | 4/2010 | Quistgaard et al. |
| 7,758,524 B2 | 7/2010 | Barthe et al. |
| 7,789,841 B2 | 9/2010 | Huckle et al. |
| 7,824,348 B2 | 11/2010 | Barthe et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,235,909 B2 | 8/2012 | Barthe et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,764,687 B2 | 7/2014 | Slayton et al. |
| 2001/0009997 A1 | 7/2001 | Pope |
| 2001/0009999 A1 | 7/2001 | Kaufman et al. |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2001/0041886 A1* | 11/2001 | Durkin ............... A61B 18/203 606/9 |
| 2002/0000763 A1 | 1/2002 | Jones |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton et al. |
| 2002/0095143 A1 | 7/2002 | Key |
| 2002/0099094 A1* | 7/2002 | Anderson ................ 514/561 |
| 2002/0115917 A1 | 8/2002 | Honda et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1* | 11/2002 | Neev ................... A61B 18/203 606/9 |
| 2002/0173721 A1 | 11/2002 | Grunwald et al. |
| 2002/0193784 A1 | 12/2002 | Mchale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0059266 A1 | 3/2004 | Fry |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishbashi et al. |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste et al. |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson |
| 2005/0091770 A1 | 5/2005 | Mourad et al. |

(56) References Cited

U.S. PATENT DOCUMENTS

| | | |
|---|---|---|
| 2005/0096542 A1 | 5/2005 | Weng et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel et al. |
| 2005/0261585 A1 | 11/2005 | Makin et al. |
| 2005/0267454 A1 | 12/2005 | Hissong |
| 2005/0288748 A1* | 12/2005 | Li et al. .................. 607/98 |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin et al. |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0100550 A1* | 5/2006 | Schultheiss ...... A61B 17/22004 601/2 |
| 2006/0111744 A1 | 5/2006 | Makin et al. |
| 2006/0116583 A1 | 6/2006 | Ogasawara et al. |
| 2006/0116671 A1 | 6/2006 | Slayton et al. |
| 2006/0122508 A1 | 6/2006 | Slayton et al. |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1 | 1/2008 | Klopotek et al. |
| 2008/0039724 A1 | 2/2008 | Seip et al. |
| 2008/0071255 A1 | 3/2008 | Barthe et al. |
| 2008/0086054 A1 | 4/2008 | Slayton et al. |
| 2008/0097253 A1 | 4/2008 | Pedersen |
| 2008/0139974 A1 | 6/2008 | Da Silva |
| 2008/0146970 A1 | 6/2008 | Litman et al. |
| 2008/0167556 A1 | 7/2008 | Thompson et al. |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton et al. |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton et al. |
| 2008/0294073 A1 | 11/2008 | Barthe et al. |
| 2008/0319356 A1 | 12/2008 | Cain et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2010/0011236 A1 | 1/2010 | Barthe et al. |
| 2010/0022919 A1 | 1/2010 | Peterson |
| 2010/0022922 A1 | 1/2010 | Barthe et al. |
| 2010/0042020 A1 | 2/2010 | Ben-Ezra |
| 2010/0049178 A1 | 2/2010 | Deem et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | Mccormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0316426 A1 | 12/2012 | Foley et al. |
| 2012/0330197 A1 | 12/2012 | Makin et al. |
| 2012/0330222 A1 | 12/2012 | Barthe et al. |
| 2012/0330223 A1 | 12/2012 | Makin et al. |

(56) References Cited

U.S. PATENT DOCUMENTS

| | | |
|---|---|---|
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018286 A1 | 1/2013 | Slayton et al. |
| 2013/0024704 A1 | 1/2013 | Barthe et al. |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211258 A1 | 8/2013 | Barthe et al. |
| 2013/0231567 A1 | 9/2013 | Barthe et al. |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310863 A1 | 11/2013 | Barthe et al. |
| 2013/0345562 A1 | 12/2013 | Barthe et al. |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0236049 A1 | 8/2014 | Barthe et al. |
| 2014/0243713 A1 | 8/2014 | Slayton et al. |
| 2014/0276055 A1 | 9/2014 | Barthe et al. |
| 2014/0316306 A1 | 10/2014 | Slayton |

FOREIGN PATENT DOCUMENTS

| | | |
|---|---|---|
| CA | 2580561 | 4/2006 |
| CA | 2583600 | 4/2006 |
| CA | 2723791 | 11/2009 |
| CA | 27478362 | 12/2009 |
| CA | 2583522 | 5/2014 |
| DE | 4029175 | 3/1992 |
| DE | 10140064 | 3/2003 |
| DE | 10219217 | 11/2003 |
| DE | 10219297 | 11/2003 |
| DE | 20314479 U1 | 2/2004 |
| DE | 20314479 U1 | 2/2004 |
| DE | 20314479 | 3/2004 |
| DE | 202005022028 | 8/2012 |
| EP | 0344773 | 12/1989 |
| EP | 1479412 | 11/1991 |
| EP | 0661029 | 12/1994 |
| EP | 0661029 A1 | 7/1995 |
| EP | 1050322 | 11/2000 |
| EP | 1234566 | 8/2002 |
| EP | 1262160 | 12/2002 |
| EP | 1374944 A | 1/2004 |
| EP | 1871479 | 4/2006 |
| EP | 1879502 | 4/2006 |
| EP | 1799305 | 6/2007 |
| EP | 1809377 | 7/2007 |
| EP | 1875327 | 1/2008 |
| EP | 2152167 | 11/2008 |
| EP | 2152351 | 11/2008 |
| EP | 2081646 | 7/2009 |
| EP | 2152367 | 2/2010 |
| EP | 1855759 | 2/2011 |
| EP | 2279696 | 2/2011 |
| EP | 2279697 | 2/2011 |
| EP | 2279698 | 2/2011 |
| EP | 2279699 | 2/2011 |
| EP | 2286874 | 2/2011 |
| EP | 09835856.7 | 7/2011 |
| EP | 2409728 | 1/2012 |
| EP | 2409729 | 1/2012 |
| EP | 2409730 | 1/2012 |
| EP | 2409731 | 1/2012 |
| EP | 2481446 | 8/2012 |
| EP | 2533130 | 12/2012 |
| EP | 2600783 | 5/2013 |
| EP | 20600937 | 5/2013 |
| EP | 2117650 | 1/2014 |
| EP | 20140082907 | 3/2014 |
| EP | 2729215 | 5/2014 |
| EP | 2731675 | 5/2014 |
| EP | 2739357 | 5/2014 |
| GB | 2113099 | 8/1983 |
| GR | DE202005022062 | 2/2013 |
| HK | 8106764.3 | 7/2007 |
| HK | 1118000 A | 1/2009 |
| HK | 8105587 | 1/2009 |
| HK | 1166474 | 11/2012 |
| IL | 181895D | 7/2007 |
| IL | 182188D | 7/2007 |
| IL | 182189D | 7/2007 |
| IL | 201942D | 11/2009 |
| IL | 201943D | 11/2009 |
| IL | 201944D | 11/2009 |
| IL | 181892 | 3/2011 |
| IL | 181895 | 6/2012 |
| IL | 182187 | 7/2014 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 11506636 | 6/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2007505793 A | 3/2007 |
| JP | 2008515557 | 5/2008 |
| JP | 2008515559 | 5/2008 |
| JP | 20058514294 | 5/2008 |
| JP | 2008522642 | 7/2008 |
| JP | 2009518126 | 5/2009 |
| JP | 20100503514 | 2/2010 |
| JP | 2010517695 | 5/2010 |
| JP | 2010526589 | 5/2010 |
| JP | 2010527644 | 8/2010 |
| JP | 2011-543684 | 6/2011 |
| JP | 2011-169651 | 8/2011 |
| JP | 4695188 B2 | 9/2011 |
| JP | 2012-24601 | 2/2012 |
| JP | 2012-75940 | 4/2012 |
| JP | 5094402 | 9/2012 |
| JP | 2013-47568 | 6/2013 |
| JP | 201347568 | 6/2013 |
| JP | 2013-171424 | 12/2013 |
| JP | 5473220 | 2/2014 |
| JP | 5485967 | 2/2014 |
| JP | 2014-87679 | 5/2014 |
| JP | 2014158953 | 9/2014 |
| KR | 1020010024871 | 3/2001 |
| KR | 1020060113930 | 11/2006 |
| KR | 1020070065332 | 6/2007 |
| KR | 2007007061 | 7/2007 |
| KR | 1020070070161 | 7/2007 |

(56) References Cited

FOREIGN PATENT DOCUMENTS

| | | |
|---|---|---|
| KR | 1020070098856 | 10/2007 |
| KR | 1020070104878 | 10/2007 |
| KR | 20070106972 | 11/2007 |
| KR | 1020070114105 | 11/2007 |
| KR | 10-2011-7016330 | 7/2011 |
| KR | 10-2011-7017978 | 7/2011 |
| KR | 10-2011-7017981 | 7/2011 |
| KR | 10-1117660 | 2/2012 |
| KR | 10-1142108 | 4/2012 |
| KR | 10-2012-7016324 | 7/2012 |
| KR | 10-2013-7005166 | 2/2013 |
| KR | 10-2013-7005168 | 2/2013 |
| KR | 10-1269918 | 5/2013 |
| KR | 10-1274569 | 6/2013 |
| KR | 20070104878 | 11/2013 |
| KR | 10-2014-7003430 | 2/2014 |
| KR | 10-2014-7003464 | 2/2014 |
| KR | 10-2014-7003515 | 2/2014 |
| TW | 97116816 | 5/2008 |
| TW | 97116818 | 5/2008 |
| WO | 9625888 | 8/1996 |
| WO | 9735518 | 10/1997 |
| WO | 9832379 | 7/1998 |
| WO | 9933520 | 7/1999 |
| WO | 9949788 | 10/1999 |
| WO | 0006032 | 2/2000 |
| WO | WO0015300 | 3/2000 |
| WO | WO0021612 | 4/2000 |
| WO | 0053113 | 9/2000 |
| WO | WO0128623 | 4/2001 |
| WO | 0182777 | 11/2001 |
| WO | WO0182778 | 11/2001 |
| WO | WO0187161 | 11/2001 |
| WO | 0209813 | 2/2002 |
| WO | WO0209813 | 2/2002 |
| WO | 0224050 | 3/2002 |
| WO | 02092168 | 11/2002 |
| WO | 03053266 A | 7/2003 |
| WO | 03065347 | 8/2003 |
| WO | WO03070105 | 8/2003 |
| WO | WO03077833 | 9/2003 |
| WO | 03086215 | 10/2003 |
| WO | 03096883 | 11/2003 |
| WO | 03099177 | 12/2003 |
| WO | 03101530 | 12/2003 |
| WO | 2004000116 A | 12/2003 |
| WO | 2004080147 | 9/2004 |
| WO | 2004110558 | 12/2004 |
| WO | 2005011804 A | 2/2005 |
| WO | 2005065408 | 7/2005 |
| WO | 2005090978 | 9/2005 |
| WO | PCT/US05/33046 | 9/2005 |
| WO | PCT/US05/33195 | 9/2005 |
| WO | PCT/US05/34358 | 9/2005 |
| WO | PCT/US05/36269 | 10/2005 |
| WO | PCT/US05/36377 | 10/2005 |
| WO | PCT/US2005/36253 | 10/2005 |
| WO | WO2006034049 | 3/2006 |
| WO | 2006036870 | 4/2006 |
| WO | 2006042163 A | 4/2006 |
| WO | 2006042168 A | 4/2006 |
| WO | 2006042201 A1 | 4/2006 |
| WO | PCT/2006/015779 | 4/2006 |
| WO | WO2006036870 | 4/2006 |
| WO | WO2006042163 | 4/2006 |
| WO | WO2006042168 | 4/2006 |
| WO | WO2006042168 A | 4/2006 |
| WO | WO2006042201 | 4/2006 |
| WO | 2006065671 | 6/2006 |
| WO | 2006082573 | 8/2006 |
| WO | WO2006116480 | 11/2006 |
| WO | 2007067563 A | 6/2007 |
| WO | PCT/US07/78712 | 9/2007 |
| WO | PCT/US2007/78945 | 9/2007 |
| WO | 2008036622 A | 3/2008 |
| WO | 2008036773 | 3/2008 |
| WO | WO2008036622 | 3/2008 |
| WO | PCT/US08/62930 | 5/2008 |
| WO | PCT/US08/62932 | 5/2008 |
| WO | PCT/US08/62936 | 5/2008 |
| WO | WO2008137942 | 11/2008 |
| WO | WO2008137944 | 11/2008 |
| WO | WO2008137948 | 11/2008 |
| WO | PCT/US09/46475 | 6/2009 |
| WO | PCT/US08/62932 | 11/2009 |
| WO | PCY/US08/62932 | 11/2009 |
| WO | PCT/US09/69467 | 12/2009 |
| WO | WO2009149390 | 12/2009 |
| WO | WO2010075547 | 7/2010 |
| WO | PCT/US11/001361 | 8/2011 |
| WO | PCT/US11/001362 | 8/2011 |
| WO | PCT/US/11/001362 | 8/2011 |
| WO | PCT/US11/001366 | 8/2011 |
| WO | PCT/US11/001367 | 8/2011 |
| WO | PCT/US/001361 | 8/2011 |
| WO | 2012018390 | 2/2012 |
| WO | WO2012018385 | 2/2012 |
| WO | WO2012018386 | 2/2012 |
| WO | WO2012018391 | 2/2012 |
| WO | WO2013009784 | 1/2013 |
| WO | WO2013009785 | 1/2013 |
| WO | WO2013009787 | 1/2013 |
| WO | WO2013012641 | 1/2013 |
| WO | WO2013048912 | 4/2013 |
| WO | WO2014055708 | 4/2014 |
| WO | WO2014145926 | 9/2014 |
| WO | WO2014145962 | 9/2014 |
| WO | WO2014146022 | 9/2014 |

OTHER PUBLICATIONS

Chen, L. et al., "Effect of Blood Perfusion on the ablation of liver perenchyma with high intensity focused ultrasound," Phys. Med. Biol; 38:1661-1673; 1993b.

Damianou et al., Application of the Thermal Dose Concept for Predicting the Necrosed Tissue Volume During Ultrasound Surgery, 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

Simon et al., "Applications of Lipid-Coated Microbubble Ultrasonic Contrast to Tumor Therapy," Ultrasound in Med. & Biol. vol. 19, No. 2, pp. 123-125 (1993).

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

U.S. Appl. No. 09/443,760, filed Nov. 19, 1999, Imaging, Therapy and Temperature Monitoring Ultrasonic System.

U.S. Appl. No. 11/744,655, filed May 4, 2007, Imaging, Therapy and Temperature Monitoring Ultrasonic System.

U.S. Appl. No. 08/943,728, filed Oct. 3, 1997, Drug Carrier.

U.S. Appl. No. 13/071,298, filed Mar. 24, 2011, Visual Imaging System for Ultrasonic Probe.

U.S. Appl. No. 12/135,962, filed Jun. 9, 2008, Method and System for Ultrasound Treatment with a Multi-Direcional Transducer.

(56) References Cited

OTHER PUBLICATIONS

U.S. Appl. No. 13/294,004, filed Nov. 10, 2011, Method and System for Ultrasound Treatment with a Multi-Directional Transducer.
U.S. Appl. No. 12/792,934, filed Jun. 3, 2010, System and Method for Ultra-High Frequency Ultrasound Treatment.
U.S. Appl. No. 12/834,754, filed Jul. 10, 2010, System and Method for Variable Depth Ultrasound Treatment.
U.S. Appl. No. 11/126,760, filed May 11, 2005, Method and System for Three-Dimensional Scanning and Imaging.
U.S. Appl. No. 12/437,726, filed May 8, 2009, Method and System for Combined Ultrasound Treatment.
U.S. Appl. No. 11/163,148, filed May 6, 2005, Method and System for Controlled Thermal Injury of Human Superficial Tissue.
U.S. Appl. No. 12/415,945, filed Mar. 31, 2009, Method and System for Nonivasive Mastopexy.
U.S. Appl. No. 11/163,152, filed Oct. 6, 2005, Method and System for Treat of Sweat Glands.
U.S. Appl. No. 11/163,154, filed Oct. 6, 2005, Method and System for Treating Cellulite.
U.S. Appl. No. 11/163,151, filed Oct. 6, 2005, Method and System for Nonivasive Face Lifts and Deep Tissue Tightening.
U.S. Appl. No. 12/028,636, filed Feb. 8, 2008, Method and System for Nonivasive Face Lifts and Deep Tissue Tightening.
U.S. Appl. No. 11/163,150, filed Oct. 6, 2005, Method and System for Photoaged Tissue.
U.S. Appl. No. 13/230,498, filed Sep. 12, 2011, Method and System for Photoaged Tissue.
U.S. Appl. No. 11/163,176, filed Oct. 7, 2005, Method and System for Treating Blood Vessel Disorders.
U.S. Appl. No. 12/350,383, filed Jan. 8, 2009, Method and System for Treating Acne and Sebaceous Glands.
U.S. Appl. No. 12/574,512, filed Oct. 6, 2009, Method and system for treating stretch marks.
U.S. Appl. No. 12/509,254, filed Jul. 24, 2009, Method and System for Enhancing Computer Peripheral Safety.
U.S. Appl. No. 11/538,794, filed Oct. 4, 2006, Ultrasound System and Method for Imaging and/or Measuring Displacement of Moving Tissue and Fluid.
U.S. Appl. No. 11/738,682, filed Apr. 23, 2007, Method and System for Non-Ablative Acne Treatment and Prevention.
U.S. Appl. No. 11/857,989, filed Sep. 19, 2007, Method and System for Treating Muscle, Tendon, Ligament and Cartilage Tissue.
U.S. Appl. No. 12/116,845, filed May 7, 2008, Method and System for Combined Energy Therapy Profile.
U.S. Appl. No. 12/116,810, filed May 7, 2008, Methods and Systems for Modulation Medicants Using Acoustic Energy.
U.S. Appl. No. 12/116,828, filed May 7, 2008, Methods and Systems for Coupling and Focusing Acoustic Energy Using a Coupler Member.
U.S. Appl. No. 12/954,484, filed Nov. 24, 2010, Methods and Systems for Generating Thermal Bubbles for Improved Ultrasound Imaging and Therapy.
U.S. Appl. No. 12/646,609, filed Dec. 23, 2009, Methods for Fat Reduction and/or Cellulite Treatment.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, Systems and Methods for Treating Cartilage.
U.S. Appl. No. 13/136,541, filed Aug. 2, 2011, Methods and Systems for Treating Plantar Fascia.
U.S. Appl. No. 13/136,544, filed Aug. 2, 2011, Systems and Methods for Ultrasound Treatment.
International Search Report and First Written Opinion.
Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.
Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.
Corry, Peter M., et al., "Human Cancer Treatment with Ultrasound", IEEE Transactions on Sonics and Ultrasonics, vol. SU-31, No. 5, Sep. 1984, pp. 444,456.
Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Husseini et al, "The Role of Cavitation in Acoustically Activated Drug Delivery," J. Control Release, Oct. 3, 2005, pp. 253-261, vol. 107(2).
Husseini et al. "Investigating the mechanism of accoustically activated uptake of drugs from Pluronic micelles," BMD Cancer 2002, 2:20k, Aug. 30, 2002, pp. 1-6.
Jenne, J., et al., "Temperature Mapping for High Energy US-Therapy", 1994 Ultrasonics Symposium, pp. 1879-1882.
Johnson, S.A., et al., "Non-Intrusive Measurement of Microwave and Ultrasound-Induced Hyperthermia by Acoustic temperature Tomography", Ultrasonics Symposium Proceedings, pp. 977-982.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al, "Miniaturized Ultrasound Arrays for Interstitial Ablation and Imaging," UltraSound Med. Biol. 2005, Nov. 1, 2005, pp. 1539-1550, vol. 31(11).
Makin et al., "Confirmal Bulk Ablation and Therapy Monitoring Using Intracorporeal Image-Treat Ultrasound Arrays", 4th International Symposium on Therapeutic Ultrasound, Sep. 19, 2004.
Manohar et al, "Photoaccoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling nad Experiments," J. Acoust. Soc. Am., Oct. 1, 2005, pp. 2715-2724, vol. 118(4).
Paradossi et al., "Poly(vinyl alcohol) as versatile biomaterial for potential biomedical applications," Journal of Materials Science: Materials in Medicine, 2003, pp. 687-691, vol. 14.
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-Induced Lesions in Canine Livers," 1999, Ultrasound in Med & Bio, vol. 25, No. 7, pp. 1099-1113.
Mitragotri, Samir; "Healing sound: the use of ultrasound in drug delivery and other therapeutic applications," Nature Reviews; Drug Delivery, pp. 255-260, vol. 4.
Sanghvi, N.T., et al., "Transrectal Ablation of Prostate Tissue Using Focused Ultrasound," 1993 Ultrasonics Symposium, IEEE, pp. 1207-1210.
Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

(56) References Cited

OTHER PUBLICATIONS

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.
Ueno, S., et al., "Ultrasound Thermometry in Hyperthermia", 1990 Ultrasonic Symposium, pp. 1645-1652.
Wang, H., et al., "Limits on Focused Ultrasound for Deep Hyperthermia", 1994 Ultrasonic Symposium, Nov. 1-4, 1994, pp. 1869-1872, vol. 3.
White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.
Sassen, Sander, "ATI's R520 architecture, the new king of the hill?" http://www.hardwareanalysis.com/content/article/1813, Sep. 16, 2005, 2 pages.
Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.
U.S. Appl. No. 12/135,962, filed Jun. 9, 2008, Method and System for Ultrasound Treatment with a Multi-Directional Transducer.
U.S. Appl. No. 11/163,148, filed Oct. 6, 2005, Method and System for Controlled Thermal Injury of Human Superficial Tissue.
U.S. Appl. No. 12/415,945, filed Mar. 31, 2009, Method and System for Noninvasive Mastopexy.
U.S. Appl. No. 11/163,152, filed Oct. 6, 2005, Method and System for Treatment of Sweat Glands.
U.S. Appl. No. 12/028,636, filed Feb. 8, 2008, Method and System for Noninvasive Face Lifts and Deep Tissue Tightening.
U.S. Appl. No. 11/163,150, filed Oct. 6, 2005, Method and System for Treating Photoaged Tissue.
U.S. Appl. No. 13/230,498, filed Sep. 12, 2011, Method and System for Treating Photoaged Tissue.
Examination Report for EPO Application No. 07853548.1-2305 dated Nov. 25, 2009.
European Examination Report in related Application No. 05808908.7 dated Jun. 29, 2009.
European Examination Report in related Application No. 05810308.6 dated Jun. 29, 2009.
European Examination Report in related Application No. 10185100.4 dated Jan. 6, 2014.
European Examination Report in related Application No. 10185120.2 dated Jan. 22, 2014.
Decision of the Korean Intellectual Property Tribunal dated Jun. 28, 2013 regarding Korean Patent No. 10-1142108, which is related to the pending and/or an application identified in the Table on the pp. 2-5 of the information Disclosure Statement herein (English translation, English translation certification, and Korean decision included).
International Search Report and Written Opinion dated Jan. 23, 2014 in Application No. PCT/US2012/046122.
International Search Report and Written Opinion dated Jan. 23, 2014 in Application No. PCT/US2012/046123.
International Search Report and Written Opinion dated Jan. 28, 2012 in Application No. PCT/US2012/046327.
International Search Report and Written Opinion dated Jan. 28, 2013 in Application No. PCT/US2012/046125.
International Search Report and Written Opinion dated Feb. 14, 2013 in Application No. PCT/US2011/001361.
International Search Report and Written Opinion dated Feb. 14, 2013 in Application No. PCT/US2011/001362.
International Search Report and Written Opinion dated Feb. 14, 2013 in Application No. PCT/US2011/001366.
International Search Report and Written Opinion dated Apr. 6, 2012 in Application No. PCT/US2011/001367.
Calderhead et al., One Mechanism Behind LED Photo-Therapy for Wound Healing and Skin Rejuvenation: Key Role of the Mast Cell, Laser Therapy, Jul. 2008, pp. 141-148, 17.3.
European Examination Report in related Application No. 09835856.7 dated Apr. 11, 2004.
International Search Report and Written Opinion dated Apr. 6, 2012 in Application No. PCT/US2011/001366.
U.S. Appl. No. 13/545,981, filed Jul. 11, 2012, System and Methods for Creating Three-Dimensionally Shaped Lesions.
U.S. Appl. No. 08/943,728, filed Oct. 3, 1997, Method and Apparatus for Safely Delivering Medicants to a Region of Tissue Using Ultrasound.
Written Opinion of the International Preliminary Examining Authority re: PCT/US2007/078712 mailed Sep. 15, 2008.

\* cited by examiner

METHOD AND SYSEM FOR NON-ABLATIVE ACNE TREATMENT AND PREVENTION

CROSS-REFERENCE TO RELATED APPLICATION

This Application claims priority to and the benefit of U.S. Provisional Patent Application No. 60/826,039 filed Sep. 18, 2006 entitled "Method and System for Non-Ablative Acne Treatment," wherein such provisional application is hereby incorporated in its entirety, by reference.

FIELD OF INVENTION

The present invention relates to treatment systems, and in particular to an ultrasound system for non-ablative treatment of acne.

BACKGROUND OF THE INVENTION

Acne vulgaris is the most common skin disease, causing temporary and permanent disfigurement. Acne typically appears on the face, back and/or chest at the onset of adrenarchy, i.e. when sex hormone activity increases in both boys and girls near puberty. Women often experience cycle-dependent acne. Acne is a disease of the sebaceous glands. Sebaceous glands are glands within the skin connected to a hair-containing canal called a follicle. The combination of the follicle and sebaceous gland is sometimes referred to as a "pilosebaceous unit." In healthy skin, the sebaceous glands produce sebum which flows out of the skin through the follicle. In diseased skin, the follicle becomes plugged with dead skin cells.

Sebum, an oily product of the sebaceous gland and cellular debris build up in the plug. Inflammation and often rupture of the hair follicles ensues, leading to gross inflammation, pus (a "whitehead"), pain, bleeding, and/or eventual scarring. If the acne lesion consists of an accumulated unruptured plug within a hair follicle, a "blackhead" forms. If the follicle ruptures superficially, a small pustule forms that often heals after a few weeks without scarring. If the follicle ruptures within the mid or deep dermis, a painful cystic abscess forms. Cystic acne usually heals with permanent and disfiguring scars.

The exact pathophysiology of acne is complex; however, several basic elements are necessary to produce an acne lesion, and acne therapies are based on attacking one or more of these basic elements. First, an active sebaceous gland is necessary. Sebaceous gland activity is driven by androgen and other sex steroid hormones. Second, a plug must form in the outflow tract of the follicle, called the infundibulum.

Bacteria, particularly *Proprionobacteria acnes* (*P acnes*) that digest sebum and follicular debris, contribute to plugging. Besides *P acnes*, numerous other strains of bacteria and other microorganisms reside within a patient's skin and contribute to the plugging. Further, tiny microorganisms besides bacteria also are typically found to reside in a patient's skin and can exacerbate acne.

The most potent treatments for acne are oral retinoids such as retinoic acid (Accutane®), which inhibit sebaceous gland function. While effective, oral retinoids such as the Accutane® drug have serious side-effects that prevent certain patients from using them. Most notably, these drugs can cause serious birth defects which prevents women of child-bearing years from using these treatments.

Many topical treatments including creams, gels, and various cleansing pads have been used to treat acne. These treatments include both over-the-counter treatments and those available only by prescription such as the Retin A® drug that is applied as a cream to the patient's body. The major drawback of topical treatments is that the creams or other substances are used up and must be constantly replaced.

Other methods and systems use various devices to treat acne which eliminates the problems of topical treatments in that devices are not used up and do not need constant replacement. Some devices pass heat through acne diseased skin or heat the surface of the skin. One such device is the Zeno™ device produced by Tyrell, Inc. of Houston, Tex. Unfortunately, these devices are not very effective, are not comfortable to use, and they cannot treat severe acne. One reason that these devices are not very effective is that they apply heat to the surface of the skin only, requiring the heat to travel down to the sebaceous gland to have any effect. It would be desirable to provide a method and system for heating the sebaceous gland directly and the area surrounding the sebaceous gland without applying unneeded heat to the patient's skin away from the sebaceous gland.

Yet other methods and systems treat acne by delivering energy to the acne diseased skin at levels that are strong enough to damage or destroy the tissue. Other techniques affect tissue by causing coagulation of the tissue, which is also effective.

Unfortunately, ablative and coagulative acne treatment methods have their drawbacks. Specifically, because they utilize enough energy to destroy or coagulate tissue, ablation and coagulation devices and techniques are generally not available over the counter for the general public's use. Therefore, it would be advantageous to provide a treatment system that is suitable for home use that can effectively treat all forms of acne, including severe acne.

It would also be advantageous to have a system and method whose use can prevent acne and/or reduce the amount of sebum production before acne flares up, or to simply to reduce skin oiliness.

SUMMARY OF THE INVENTION

A method and system for non-ablative treatment and prevention of acne are provided. In an exemplary embodiment, focused, unfocused or defocused ultrasound energy is applied to a region of interest to treat acne. An exemplary method and system are configured for targeted treatment of a pilosebaceous unit, particularly the sebaceous glands and their contents, in various manners, such as through use of therapy only, therapy and monitoring, imaging and therapy, or therapy, imaging, and monitoring. Targeted therapy of sebaceous glands can be provided through use of unfocused, focused, or defocused ultrasound energy at various spatial and temporal energy settings.

An exemplary method and system are configured to heat a region of interest approximately 1-10 millimeters below the surface of the patient's skin by applying unfocused or defocused ultrasound energy to the region of interest. In one exemplary embodiment ultrasound energy is applied at known depths over an extended area without initial or ongoing imaging.

In an exemplary embodiment, the heating occurs approximately 1-5 millimeters below the surface of the patient's skin and raises the temperature at this depth in a range of approximately 1°-25° C. higher than the patient's normal body temperature and causes certain mechanical effects at the region of interest to treat acne. In an exemplary embodiment, the temperature increase is between 1°-15° C. higher than the patient's normal body temperature. Therefore, the heating occurs at the depth of the sebaceous glands and not at the surface of the skin away from the sebaceous glands. Therefore, the temperature at the specific depths in the region of interest is raised between approximately 35°-49° C. In an alternative exemplary embodiment, the temperature within the region of interest can be raised between the range of approximately 35°-60° C. Other temperature ranges can be used though and fall within the scope of the invention.

In an exemplary embodiment, enough energy is emitted from the ultrasound system to stay below the thermal capacity of the tissue. Therefore, no ablation or coagulation of the tissue occurs. In certain exemplary embodiments, the temperature increase may be dramatic, but if it is only applied for a short period of time the overall application of energy will be low enough so that no ablation or coagulation of the issue occurs. In other embodiments, the temperature increase may be small but applied over a longer time period to properly affect the sebaceous glands without ablation or coagulation occurring. Essentially, the time averaged power or thermal dose stays below a level where ablation or coagulation occurs.

Heating the region of interest at these depths causes one or more physiological effects that treat acne. In an exemplary embodiment, the heat causes increased blood perfusion in the region of interest. Additionally, the heat raises the temperature to a level where proteins within the region of interest are denatured.

Further, heat can initiate programmed cell death or apoptosis of bacteria cells that contribute to acne. Programmed cell death is the natural process where cells produce certain chemicals that lead to the cell's death. Applying heat to an acne infested region of interest can cause bacteria cells (such as P acnes) to produce those chemicals and initiate programmed cell death of bacteria cells which further reduces acne. Finally, the application of energy can decrease sebum production by the application of heat and various mechanical effects at the region of interest.

In an exemplary embodiment treatment is used to prevent acne from occurring. In an exemplary embodiment treatment is used to suppress the activity of sebaceous glands, thereby reducing the size and number of skin pores, decreasing skin oiliness, and achieving a desirable cosmetic effect.

In an exemplary embodiment, an exemplary system comprises an ultrasound system that emits ultrasound energy at concentrated levels to the region of interest at specific or targeted depths beneath the patient's skin to heat the region of interest as described above. An exemplary ultrasound system comprises a control system, a probe, and a display or indicator system. The probe can comprise various probe and/or transducer configurations. In an exemplary embodiment, the probe delivers unfocused ultrasound energy to the region of interest without performing an imaging function. In other exemplary embodiments, the probe delivers strongly focused or weakly focused ultrasound energy. In yet other exemplary embodiments, imaging can be completed during treatment. In other exemplary embodiments, the probe can be configured for a combined dual-mode imaging/therapy transducer, coupled or co-housed imaging/therapy transducers, or simply a therapy probe or an imaging probe.

The control system and display system can also comprise various configurations for controlling probe and system functionality, including for example a microprocessor with software and a plurality of input/output devices, a system for controlling electronic and/or mechanical scanning and/or multiplexing of transducers, a system for power delivery, systems for monitoring, systems for sensing the spatial position of the probe and/or transducers, and systems for handling user input and recording treatment results, among others.

In an exemplary embodiment, a coupling agent, containing at least one of a gel, cream, liquid, emulsion, medicant or other compound is used to acoustically couple the probe to a patient's body. In an exemplary embodiment, the coupling agent contains medicines and other drugs that are delivered to the patient's body during the emission of energy from the probe. In this exemplary embodiment, the drugs and medicines within the agent are directed at skin treatment and repair for treating diseases such as acne.

BRIEF DESCRIPTION OF THE DRAWINGS

The subject matter of the invention is particularly pointed out in the concluding portion of the specification. The invention, however, both as to organization and method of operation, may be best understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a method and system for treating acne and sebaceous glands and the prevention of acne as described herein are merely indicative of exemplary applications for the invention. For example, the principles, features and methods discussed may be applied to any medical application. Further, various aspects of the present invention may be suitably applied to other applications. Moreover, references to "sebaceous gland" include not just the gland itself, but all the contents within the gland.

Figure 1:
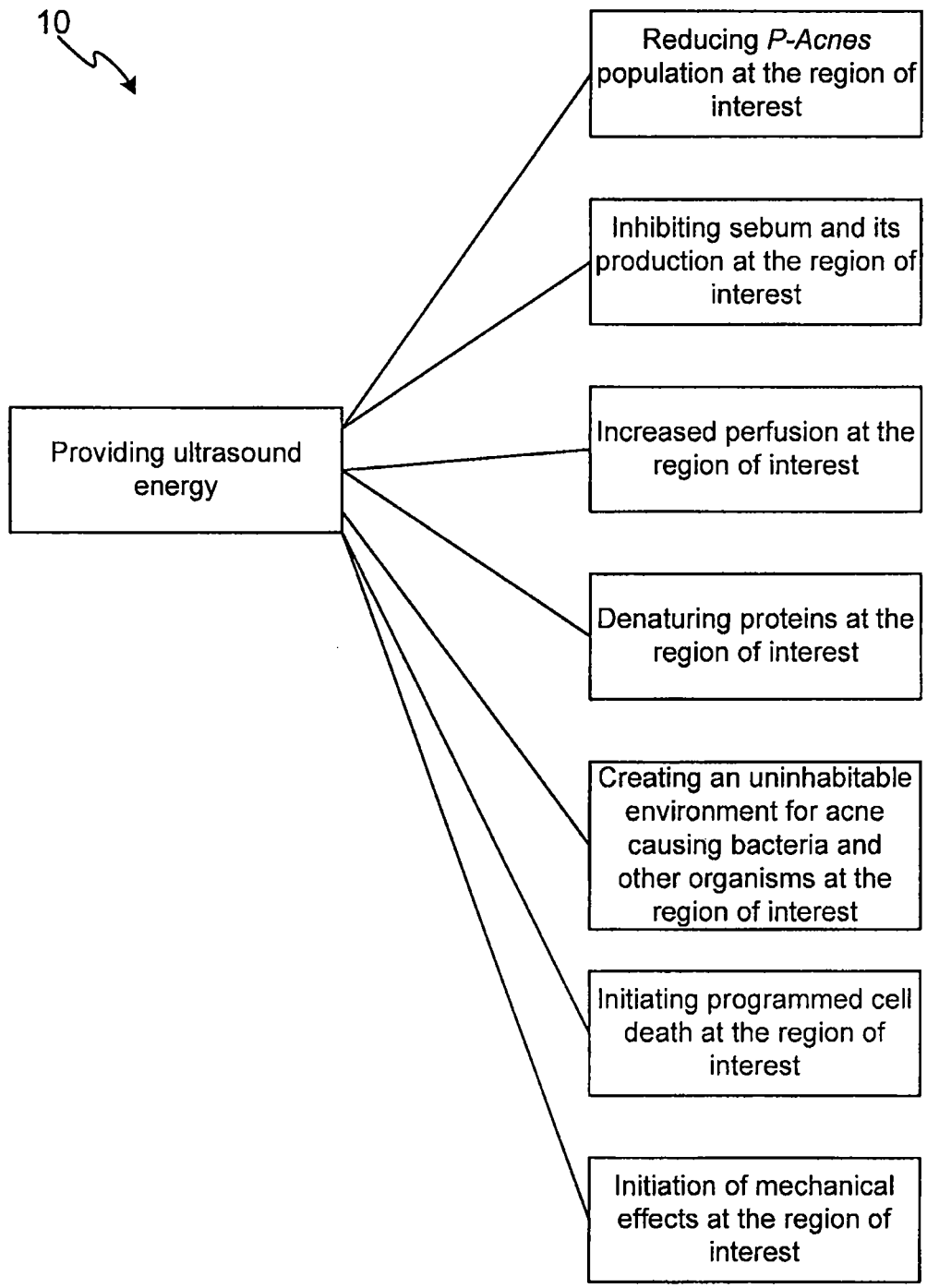
FIG. 1 illustrates a block diagram of the method of acne treatment in accordance with an exemplary embodiment of the present invention

With reference to FIG. 1, the method of treating existing acne and preventing future acne comprises targeting energy to a region of interest that comprises a pilosebaceous unit and its contents. In an exemplary embodiment, the energy is ultrasound energy. In other exemplary embodiments, the energy is microwave energy, radio frequency energy, light energy, or other energy forms.

This method will be generally referred to as method 10 throughout and produces numerous physiological effects such as increased blood perfusion, the denaturing of proteins, causing various mechanical effects, creating an uninhabitable environment for acne contributing bacteria and organisms, and accelerating the programmed cell death of bacteria and other acne causing organisms. These physiological effects occur at a region of interest 12 (ROI 12). Any of these physiological effects at ROI 12 treat current acne and prevent future acne from occurring at ROI 12.

ROI 12 can comprise an inner treatment region, a superficial region, a subcutaneous region of interest and/or any other region of interest in between an inner treatment region, a superficial region, and/or a subcutaneous region within a patient. In various exemplary embodiments, ROI 12 comprises at least one pilosebaceous unit 68 and an associated sebaceous gland 70. Throughout this application, reference to a "pilosebaceous unit 68" includes all the contents of the pilosebaceous unit 68 and related sebaceous gland 70.

Further, while only one ROI 12 is depicted, a plurality of ROI 12 can be treated by system 14 within an exemplary non-ablative acne treatment method. Also, while the present invention is directed at ROI 12 with a pilosebaceous unit 68 and sebaceous gland 70, method 10 can also be used to treat other glands beside sebaceous glands 70.

Other glands besides sebaceous glands capable of being treated by method 10 include sweat glands, endocrine glands, and other glands within mammalian bodies. Therefore, method 10 can be used to treat oily hair and skin as well as other ailments besides acne by the methods and systems discussed herein.

Applying ultrasound energy 72 at ROI 12 raises the temperature within ROI 12 without causing ablation or coagulation of tissue within ROI 12. The increase in temperature causes numerous physiological effects to treat current acne and prevent future acne from occurring. First, in response to the increased temperature caused by ultrasound energy 72 provided from a system 14 configured to emit energy such as ultrasound energy 72, the body sends more blood to ROI 12 in an attempt to cool ROI 12. The increased blood perfusion delivers more blood to the ROI 12. The increased blood at ROI 12 results in increased number of repair cells contained within the blood to be delivered to ROI 12. Specifically, the more blood that flows to ROI 12, the more fibroblast cells and other therapeutic leucocyte cells (white blood cells) such as lymphocytes, macrophages, and neutrophils are at ROI 12 to treat current acne and prevent future acne from developing. The repair cells treat existing acne by helping acne lesions heal faster. Future acne is prevented because more nutrients at ROI 12 are able to fight acne-causing bacteria such as P-acnes.

Further, the increased temperature of ROI 12 is high enough to where proteins are denatured within the ROI 12. The proteins within ROI 12 that are denatured are the same proteins that P acnes and other acne causing microorganisms eat as a food source. Destroying these proteins by denaturing them eliminates P acnes' food supply contributing to the destruction of these bacteria.

The denatured proteins and increased temperature of ROI 12 create an environment that is uninhabitable for P acnes, other bacteria and microorganisms that contribute to acne. In an exemplary embodiment, the uninhabitable environment is non-life sustaining for P acnes and other organisms that contribute to acne. These parasites die which also reduces current acne (both mild and severe acne) within patients and prevents acne from forming initially.

Another physiological effect caused by heating ROI 12 is programmed cell death. While programmed cell death occurs at a natural rate, that rate can be increased by applying heat at non-ablative and non-coagulative levels to ROI 12. Specifically, heat activates certain genes that are responsible for the production of lethal chemicals. These lethal chemicals cause bacteria cells to die in programmed cell death. Heating ROI 12 causes the bacteria to create the lethal chemicals faster than they normally would and effectuates programmed cell death. In an exemplary embodiment, the bacteria are P-acnes and the programmed cell death of P-acnes cells reduces existing acne and prevents further acne from developing.

Yet another physiological effect is the inhibition of sebum and its production. Sebum and sebum production is inhibited not only by the targeted heat created at ROI 12, but also certain mechanical effects of ultrasound energy 72 has on sebaceous glands 70 and the cells that comprise sebaceous glands 70. The heat, although non-ablative and non-coagulative, causes certain effects to the cells that comprise the sebaceous glands 70. Specifically, heat reduces the cells viability and therefore reduces the sebaceous gland's ability to produce sebum. For example, heating ROI 12 to approximately 52° C. for approximately eight seconds can reduce the viability of certain cells that comprise the sebaceous glands.

Ultrasound also produces certain mechanical effects on sebaceous glands 70. In an exemplary embodiment, these mechanical effects comprise cavitation, streaming and sheer stress on cellular membranes of cells that comprise sebaceous glands 70. These mechanical effects such as cavitation and streaming create various forces that contact cellular walls of P-acnes and other acne causing organisms which damage or kill them. Further, these mechanical effects can also help drive medicinal creams and other agents into cells to better effectuate treatment as described below. Again, while these mechanical effects are neither ablative nor coagulative, they do cause damage or stress on cells critical to sebum production. This stress reduces the cells' ability to produce an active sebaceous gland 70 and sebum production is inhibited or reduced significantly.

These physiological effects at ROI 12 create an uninhabitable environment for acne-causing bacteria such as P-acnes and other acne-causing or contributing organisms at ROI 12. Creating this uninhabitable environment reduces the bacteria at ROI 12, specifically the P-acnes population at ROI 12 which treats existing acne and prevents future acne from developing.

Figure 2:
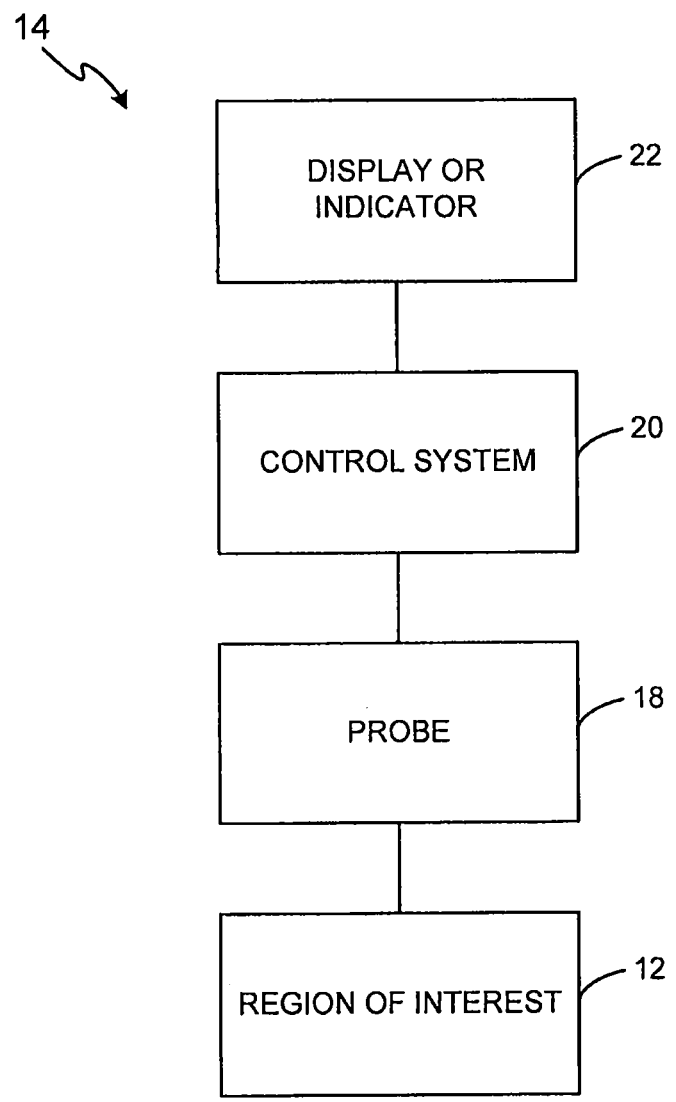
FIG. 2 illustrates a block diagram of a treatment system in accordance with an exemplary embodiment of the present invention.

An exemplary system 14 for non-ablative acne treatment is provided and depicted in FIG. 2. Unlike devices that raise the temperate of the skin, method 10 and system 14 are configured to raise the temperature below the surface of the skin and apply heat to the direct area where needed. In an exemplary embodiment, with reference to FIG. 3, an ultrasound system 16 comprising a probe 18, a control system 20, and a display system 22 is used to delivery energy to and monitor ROI 12. Other exemplary systems are disclosed in co-pending U.S. patent application Ser. No. 11/163,177 entitled "Method and System For Treating Acne and Sebaceous Glands" and U.S. patent application Ser. No. 10/950,112 entitled "Method and System For Combined Ultrasound Treatment", both of which are hereby incorporated by reference.

Figure 4:
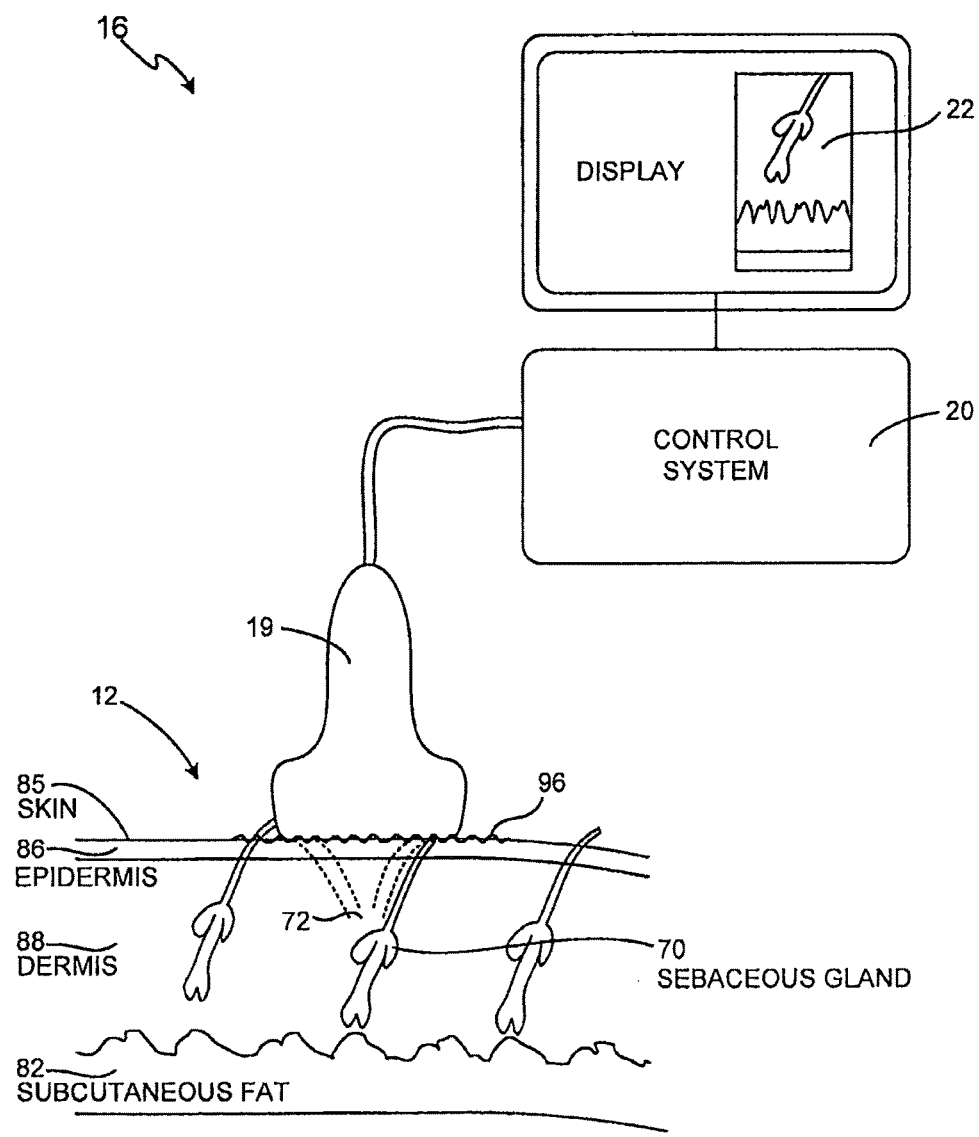
FIG. 4 illustrates a schematic diagram of an ultrasound treatment system configured to both treat the pilosebaceous unit and be used to assist in drug delivery in accordance with an exemplary embodiment of the present invention.

With additional reference to FIG. 4, an exemplary probe 18 is a transducer 19 that emits ultrasound energy 72 into ROI 12 to heat ROI 12 at a specific depth to target pilosebaceous unit 68 and sebaceous gland 70. A coupling agent is used to couple probe 18 to a patient's body in one exemplary embodiment.

In another exemplary embodiment, suction is used to attach probe 18 to the patient's body. In this exemplary embodiment, a negative pressure differential is created and probe 18 attaches to skin 85 by suction. A vacuum-type device is used to create the suction and the vacuum device can be integral with, detachable, or completely separate from probe 18. The suction attachment of probe 18 to skin 85 and associated negative pressure differential ensures that probe 18 is properly coupled to skin 85. Further, the suction-attachment also reduces the thickness of the tissue to make it easier to reach pilsobaceous unit 68.

Figure 5A:
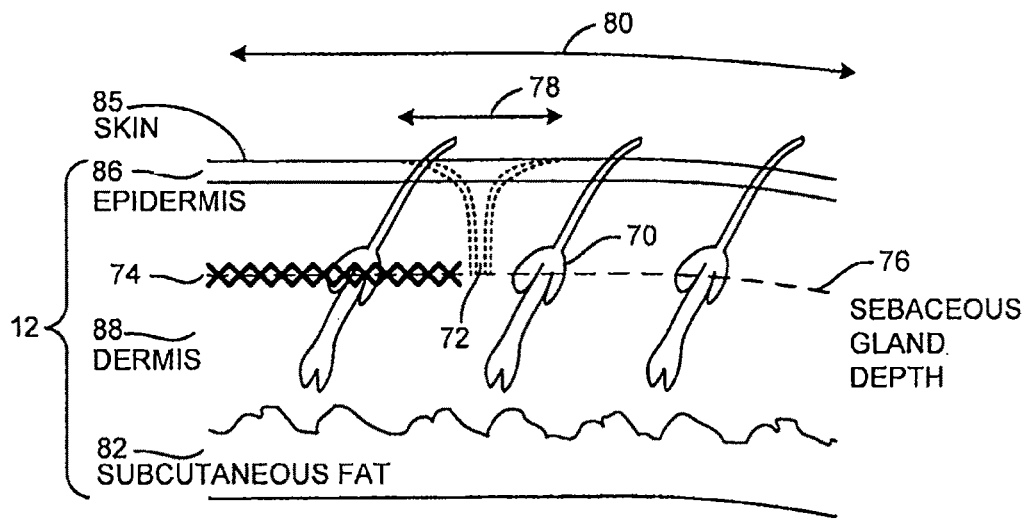
FIGS. 5A-5B illustrate schematic diagrams of ultrasound treatment systems configured to treat the sebaceous gland via direct targeting within the treatment layer in accordance with various exemplary embodiments of the present invention.
Figure 5B:
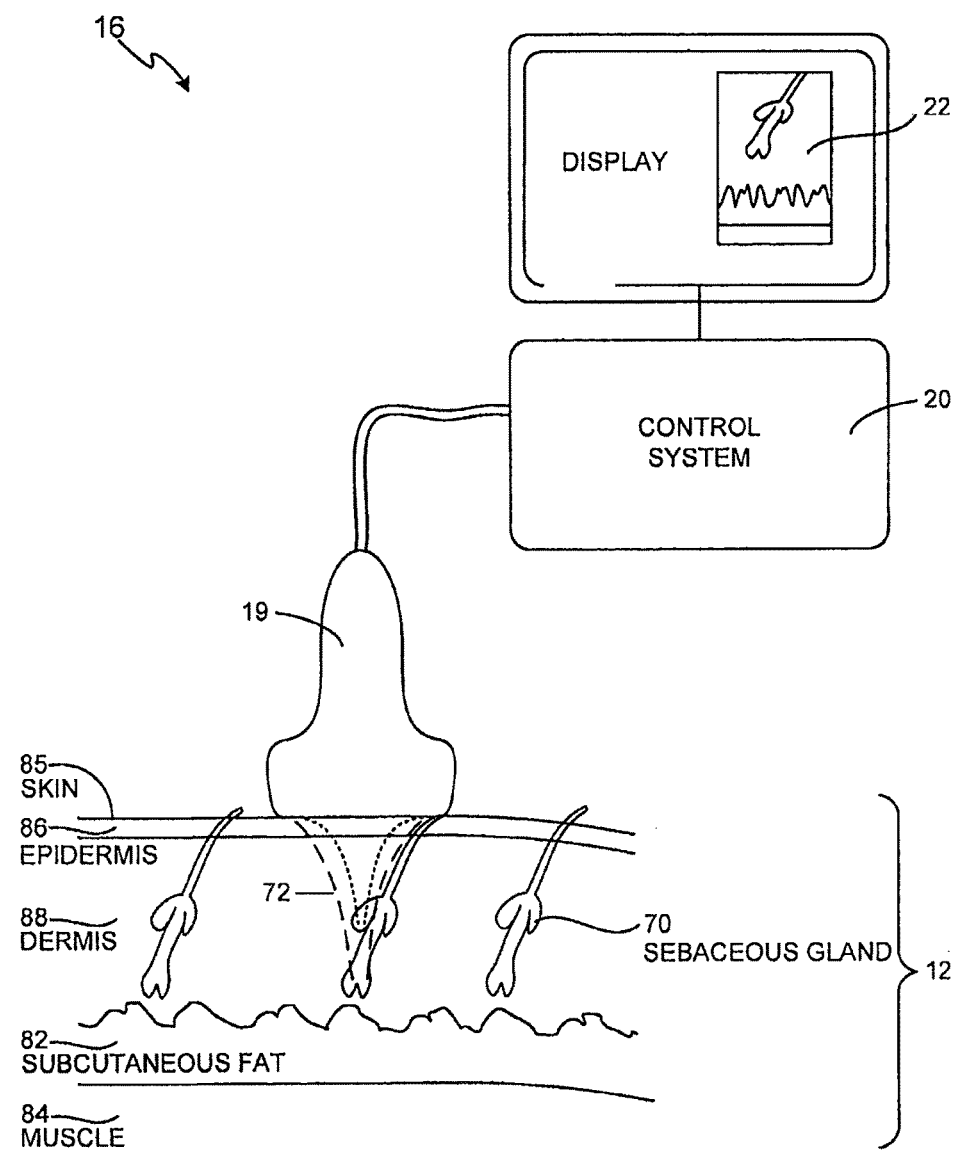

With additional reference to FIGS. 5A and 5B, ultrasound energy 72 can be emitted in various energy fields 73 in this exemplary embodiment. Energy fields 73 can be focused, defocused, and/or made substantially planar by transducer 19 to provide a plurality of different effects. Energy can be applied at one or more points in one or more C-planes or C-scans by automated or manual movement. For example, a substantially planar energy field can provide a heating and/or pretreatment effect, a focused energy field can provide a more concentrated source of heat or hyperthermal effect, and a non-focused energy field can provide diffused heating effects. It should be noted that the term "non-focused" as used throughout is meant to encompass energy that is unfocused or defocused.

An exemplary transducer 19 emits ultrasound energy for imaging or treatment or a combination of both imaging and treatment. In an exemplary embodiment, transducer 19 is configured to emit ultrasound energy at specific depths in ROI 12 as described below. In this exemplary embodiment of FIG. 5A, transducer 19 emits unfocused or defocused ultrasound energy over a wide area in ROI 12 for treatment purposes.

With continued reference to FIG. 4, transducer 19 can comprise one or more transducers configured for facilitating treatment. Transducer 19 can also comprise one or more transduction elements 26, e.g., elements 26A or 26B. The transduction elements 26 can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 19 can comprise any other materials configured for generating radiation and/or acoustical energy. Transducer 19 can also comprise one or more matching and/or backing layers configured along with transduction element 26 such as coupled to the piezoelectrically active material. Transducer 19 can also be configured with single or multiple damping elements along transduction element 26.

In accordance with an exemplary embodiment, the thickness of transduction element 26 of transducer 19 can be configured to be uniform. That is, transduction element 26 can be configured to have a thickness that is substantially the same throughout. In accordance with another exemplary embodiment, transduction element 26 can also be configured with a variable thickness, and/or as a multiple damped device. For example, transduction element 26 of transducer 19 can be configured to have a first thickness selected to provide a center operating frequency of a lower range, for example from approximately 1 kHz to 3 MHz. Transduction element 26 can also be configured with a second thickness selected to provide a center operating frequency of a higher range, for example from approximately 3 to 100 MHz or more.

Transducer 19 can be configured as a single broadband transducer excited with at least two or more frequencies to provide an adequate output for raising the temperature within ROI 12 to the desired level. Transducer 19 can also be configured as two or more individual transducers, wherein each transducer 19 comprises transduction element 26. The thickness of transduction elements 26 can be configured to provide center-operating frequencies in a desired treatment range. For example, transducer 19 can comprise a first transducer 19 configured with a first transduction element 26 having a thickness corresponding to a center frequency range of approximately 1 MHz to 3 MHz, and a second transducer 19 configured with a second transduction element 26 having a thickness corresponding to a center frequency of approximately 3 MHz to 100 MHz or more. Various other ranges of thickness for a first and/or second transduction element 26 can also be realized.

Moreover, in an exemplary embodiment, any variety of mechanical lenses or variable focus lenses, e.g. liquid-filled lenses, may also be used to focus and or defocus the energy field. For example, with reference to exemplary embodiments depicted in FIGS. 6A and 6B, transducer 19 may also be configured with an electronic focusing array 24 in combination with one or more transduction elements 26 to facilitate increased flexibility in treating ROI 12. Array 24 may be configured in a manner similar to transducer 19. That is, array 24 can be configured as an array of electronic apertures that may be operated by a variety of phases via variable electronic time delays, for example, $\tau_1, \tau_2, \tau_3 \ldots \tau_j$. By the term "operated," the electronic apertures of array 24 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 12.

Transduction elements 26 may be configured to be concave, convex, and/or planar. For example, in an exemplary embodiment depicted in FIG. 6A, transduction elements 26A are configured to be concave in order to provide focused energy for treatment of ROI 12. Additional embodiments are disclosed in U.S. patent application Ser. No. 10/944,500, entitled "System and Method for Variable Depth Ultrasound Treatment", and again incorporated herein by reference.

Figure 6A:
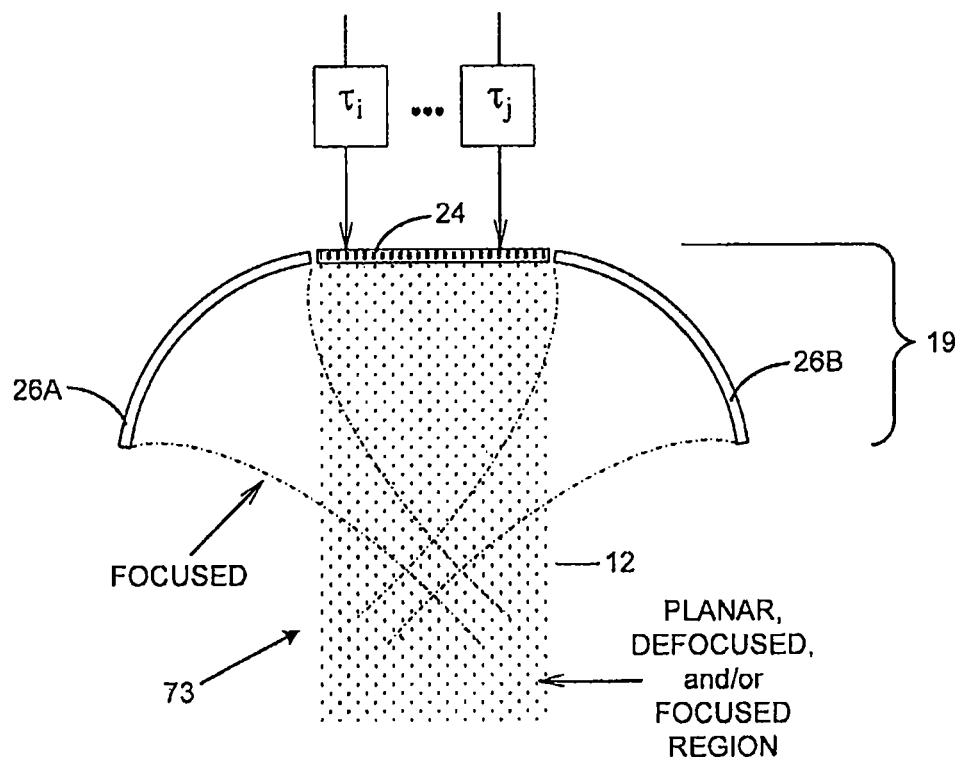
FIGS. 6A, 6B, 6C, 6D, and 6E illustrate cross-sectional diagrams of an exemplary transducer in accordance with various embodiments of the present invention.
Figure 6B:
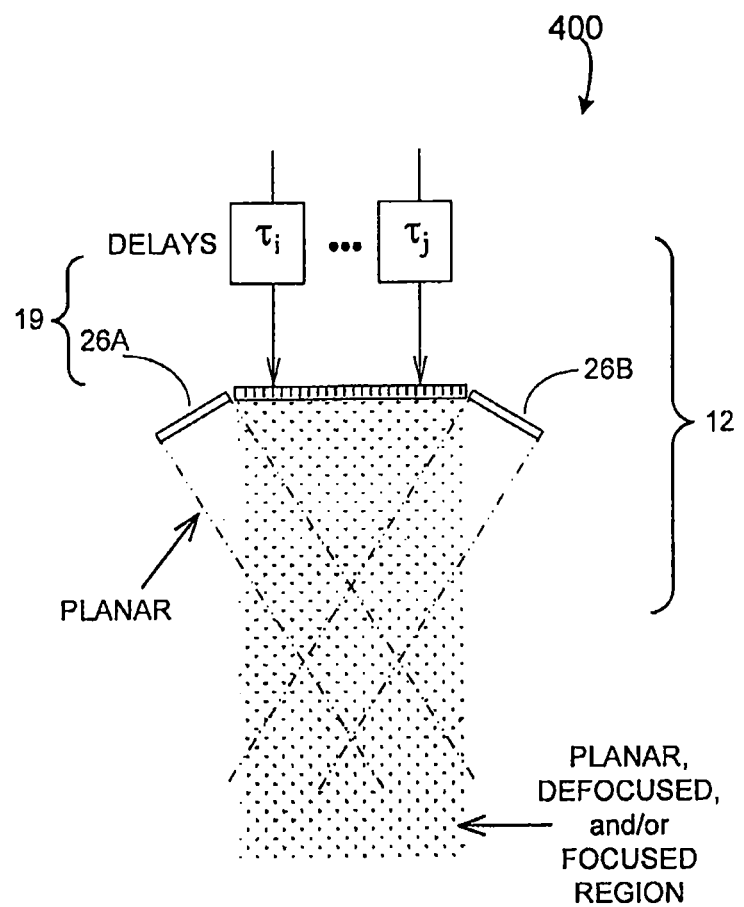

In another exemplary embodiment, depicted in FIG. 6B, transduction elements 26A and 26B can be configured to be substantially flat in order to provide substantially uniform energy to ROI 12. While FIGS. 6A and 6B depict exemplary embodiments with transduction elements 26 configured as concave and substantially flat, respectively, transduction elements 26 can be configured to be concave, convex, and/or substantially flat. In addition, transduction elements 26 can be configured to be any combination of concave, convex, and/or substantially flat structures. For example, a first transduction element 26 can be configured to be concave, while a second transduction element 26 can be configured to be substantially flat.

Figure 6C:
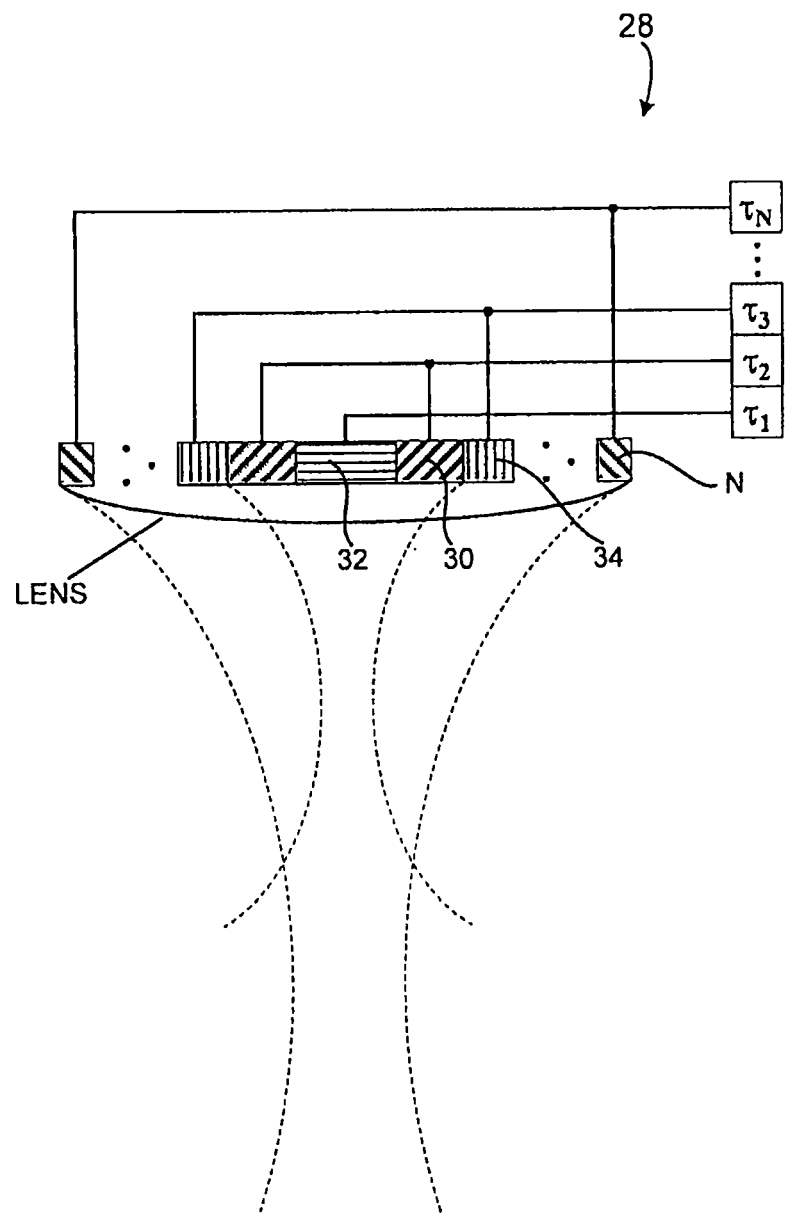
Figure 6D:
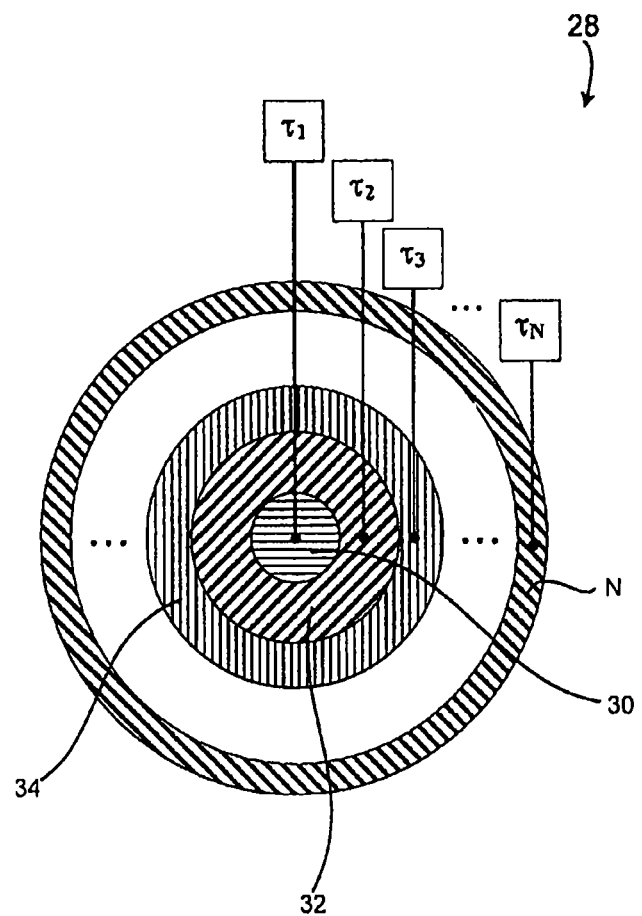

With reference to FIGS. 6C and 6D, transducer 19 can also be configured as an annular array to provide planar, focused and/or defocused acoustical energy. For example, in accordance with an exemplary embodiment, an annular array 28 can comprise a plurality of rings 30, 32, 34 to N. Rings 30, 32, 34 to N can be mechanically and electrically isolated into a set of individual elements, and can create planar, focused, or defocused waves. For example, such waves can be centered on-axis, such as by methods of adjusting corresponding transmit and/or receive delays, $\tau_1$, $\tau_2$, $\tau_3$ . . . $\tau_N$. An electronic focus can be suitably moved along various depth positions, and can enable variable strength or beam tightness, while an electronic defocus can have varying amounts of defocusing. In accordance with an exemplary embodiment, a lens and/or convex or concave shaped annular array 28 can also be provided to aid focusing or defocusing such that any time differential delays can be reduced. Movement of annular array 28 in one, two or three-dimensions, or along any path, such as through use of probes and/or any conventional robotic arm mechanisms, may be implemented to scan and/or treat a volume or any corresponding space within ROI 12.

Figure 6E:
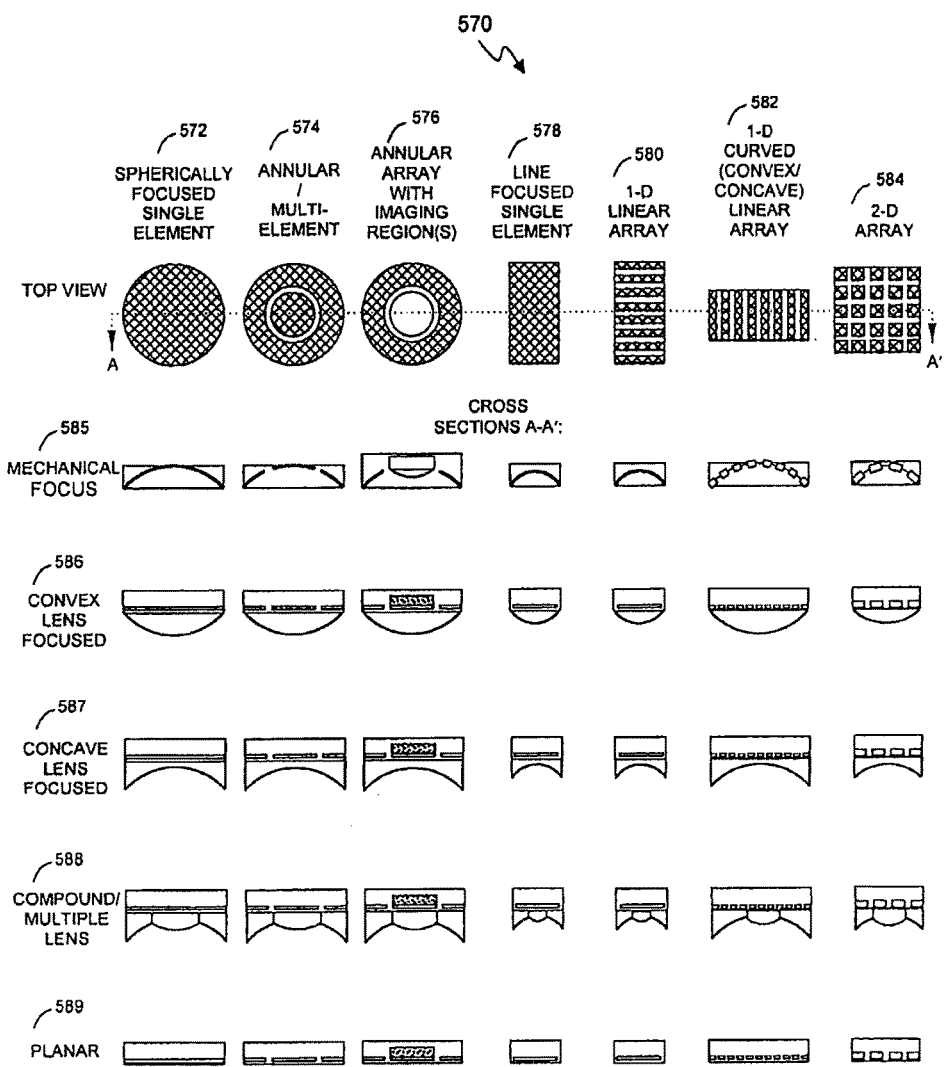

With reference to FIG. 6E, an exemplary transducer 570 can also be configured as a spherically focused single element 572, annular/multi-element 574, annular with imaging region(s) 576, line-focused single element 578, 1-D linear array 580, 1-D curved (convex/concave) linear array 582, and/or 2-D array 584, with mechanical focus 585, convex lens focus 586, concave lens focus 587, compound/multiple lens focused 588, and/or planar array form 589 to achieve focused, unfocused, or defocused sound fields for both imaging and/or therapy. In certain exemplary embodiments, spherical lens are used in treating acne and cylindrical lenses are used for preventing acne at ROI 12. Other lens shapes can still be used in other exemplary embodiments of the present invention.

Figure 7A:
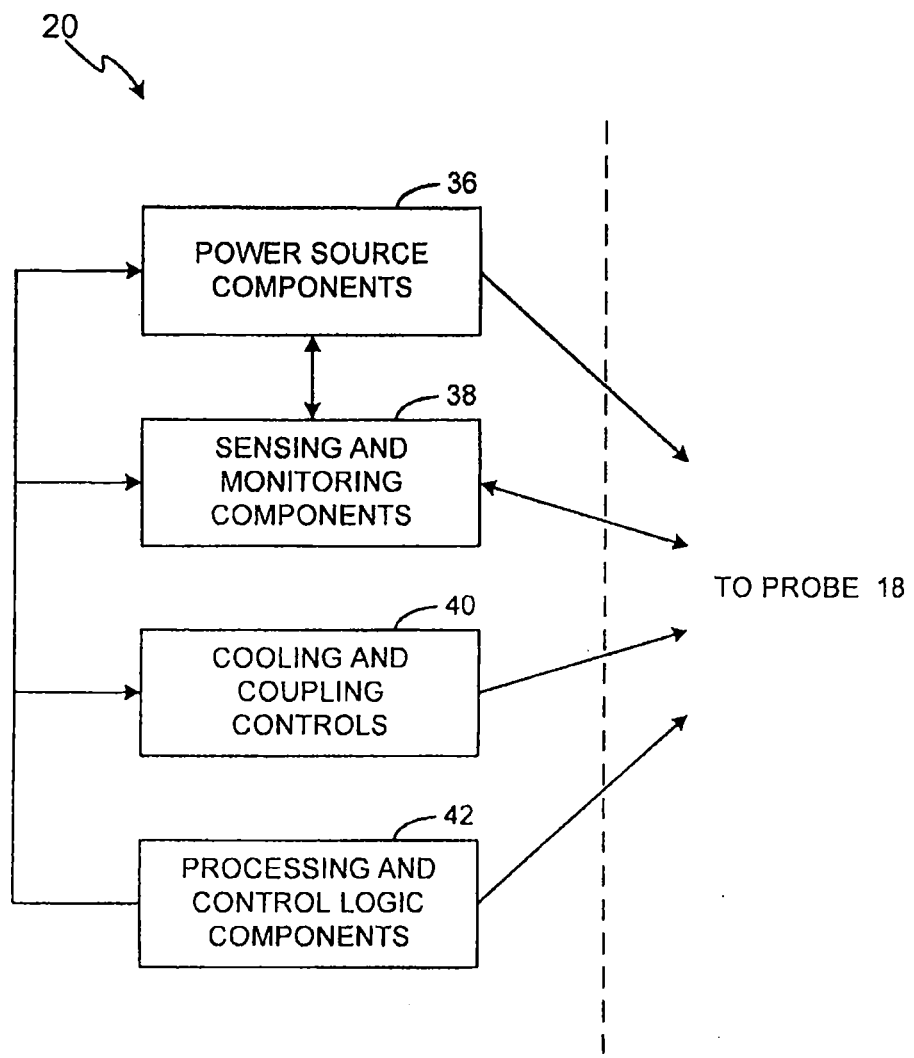
FIGS. 7A, 7B, and 7C illustrate block diagrams of an exemplary control system in accordance with exemplary embodiments of the present invention
Figure 7B:
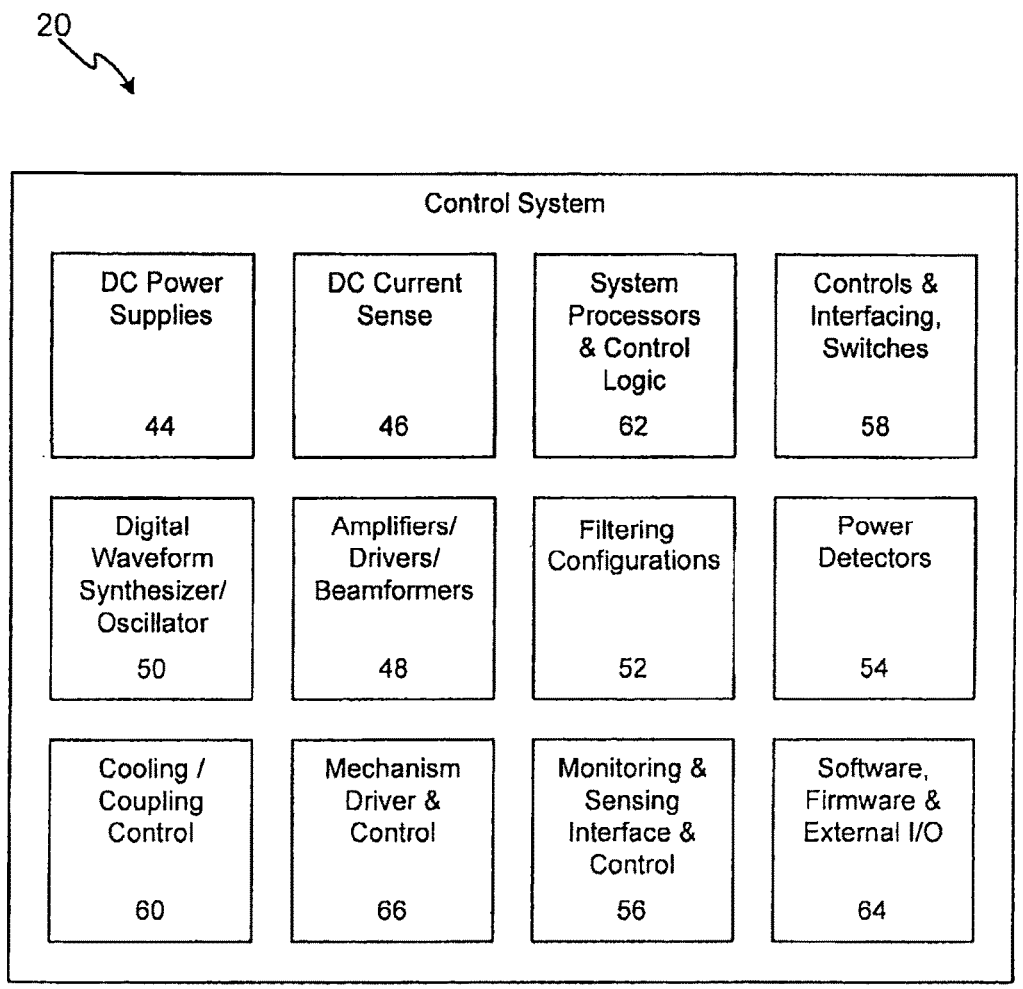

An exemplary transducer is suitably controlled and operated in various manners by control system 20. In an exemplary embodiment depicted in FIGS. 7A-7C, control system 20 is configured for coordination and control of the entire acne treatment process to achieve the desired therapeutic effect by targeting sebaceous glands 70 within ROI 12. For example, control system 20 can suitably comprise power source components 36, sensing and monitoring components 38, cooling and coupling controls 40, and/or processing and control logic components 42. Control system 20 can be configured and optimized in a variety of ways with more or less subsystems and components to implement the therapeutic system for controlled targeting of the pilosebaceous unit 68 and sebaceous glands 70, and the embodiments in FIGS. 6A and 6B are merely for illustration purposes.

For example, for power sourcing components 36, control system 20 can comprise one or more direct current (DC) power supplies 44 configured to provide electrical energy for entire control system 20, including power required by a transducer electronic amplifier/driver 48. A DC current sense device 46 can also be provided to confirm the level of power going into amplifiers/drivers 48 for safety and monitoring purposes.

Amplifiers/drivers 48 can comprise multi-channel or single channel power amplifiers and/or drivers. In accordance with an exemplary embodiment for transducer array configurations, amplifiers/drivers 48 can also be configured with a beamformer to facilitate array focusing. An exemplary beamformer can be electrically excited by an oscillator/digitally controlled waveform synthesizer/oscillator 50 with related switching logic.

Power sourcing components 36 can also include various filtering configurations 52. For example, switchable harmonic filters and/or matching may be used at the output of amplifier/driver/beamformer 48 to increase the drive efficiency and effectiveness. Power detection components 54 may also be included to confirm appropriate operation and calibration. For example, electric power and other energy detection components 54 may be used to monitor the amount of power going to probe 18.

Various sensing and monitoring components 38 may also be suitably implemented within control system 20. For example, in accordance with an exemplary embodiment, monitoring, sensing and interface control components 56 may be configured to operate with various motion detection systems implemented within transducer 19 to receive and process information such as acoustic or other spatial and temporal information from ROI 12. Sensing and monitoring components 38 can also include various controls, interfacing and switches 58 and/or power detectors 54. Such sensing and monitoring components 38 can facilitate open-loop and/or closed-loop feedback systems within treatment system 14.

In an exemplary embodiment, sensing and monitoring components 38 comprise a sensor that is connected to an audio or visual alarm system to prevent overuse of system 14. In this exemplary embodiment, the sensor senses the amount of energy transferred to skin 85 or the time that system 14 has be actively emitting energy. When a certain time or temperature threshold has been reached, the alarm sounds an audible alarm or causes a visual indicator to activate to alert the user that the threshold is reached. This prevents the user from overusing system 14. In an exemplary embodiment, the sensor could be operatively connected to control system 20 and force control system 20 to stop emitting ultrasound energy 72 from probe 18.

A cooling/coupling control systems 60 may be provided to remove waste heat from an exemplary probe 18, provide a controlled temperature at the superficial tissue interface and deeper into tissue, and/or provide acoustic coupling from probe 18 to ROI 12. Such cooling/coupling control systems 60 can also be configured to operate in both open-loop and/or closed-loop feedback arrangements with various coupling and feedback components.

Additionally, an exemplary control system 20 can further comprise various system processor and digital control logic 62, such as one or more control or interfacing switches 58 and associated components, including firmware and control software 64, which interfaces to user controls and interfacing circuits as well as input/output circuits and systems for communications, displays, interfacing, storage, documentation, and other useful functions. System software 64 controls all initialization, timing, level setting, monitoring, safety monitoring, and all other system functions required to accomplish user-defined treatment objectives. Further, various control switches 66 can also be suitably configured to control operation.

Figure 7C:
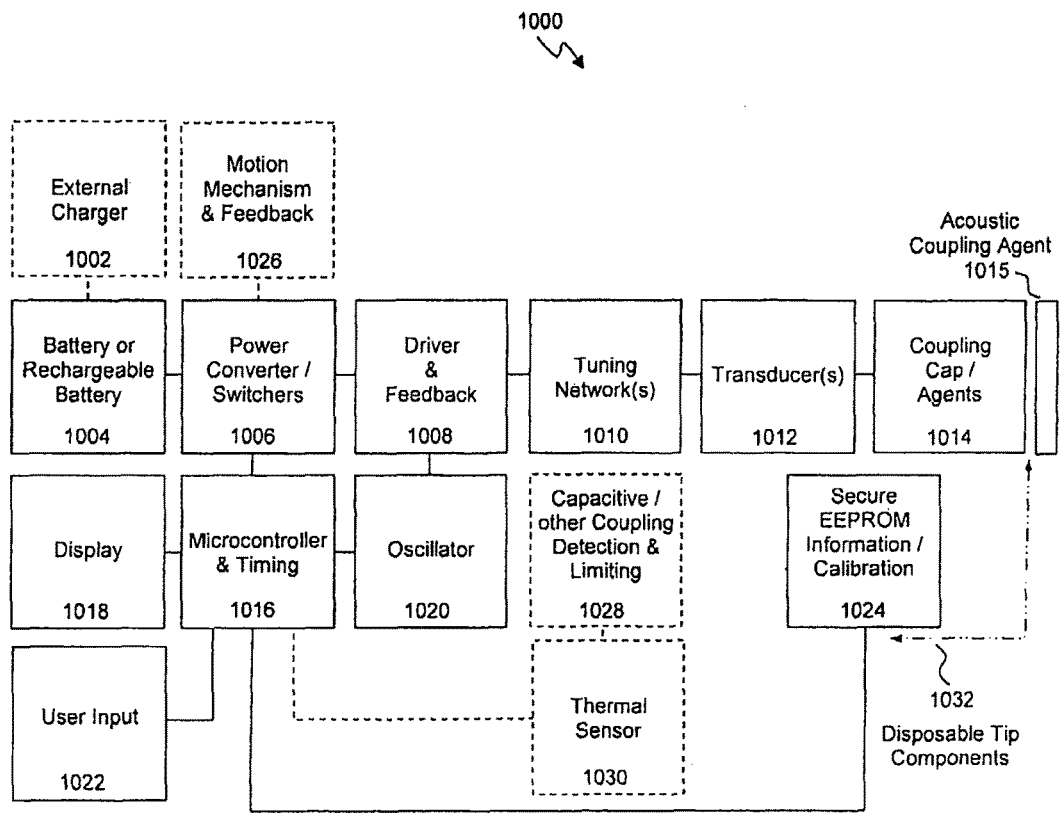

With reference to FIG. 7C, an exemplary transducer is suitably controlled and operated in various manners by a hand-held format control system 1000. An external battery charger 1002 can be used with rechargeable-type batteries 1004 or batteries 1004 can be single-use disposable types, such as AA-sized cells. Power converters 1006 produce voltages suitable for powering a driver/feedback circuit 1008 with tuning network 1010 driving a transducer 1012 coupled to the patient via one or more acoustic coupling caps 1014. The cap 1014 can be composed of at least one of a solid media, semi-solid e.g. gelatinous media, and/or liquid media equivalent to an acoustic coupling agent (contained within a housing). The cap 1014 is coupled to the patient with an acoustic coupling agent 1015. In addition, a microcontroller and timing circuits 1016 with associated software and algorithms provide control and user interfacing via a display 1018, oscillator 1020, and other input/output controls 1022 such as switches and audio devices. A storage element 1024, such as an EEPROM, secure EEPROM, tamper-proof EEPROM, or similar device holds calibration and usage data. A motion mechanism with feedback 1026 can be suitably controlled to scan the transducer, if desirable, in a line or two-dimensional pattern and/or with variable depth. Other feedback controls include a capacitive, acoustic, or other coupling detection means and/or limiting controls 1028 and thermal sensor 1030. A combination of the secure EEPROM with at least one of coupling caps 1014, transducer 1012, thermal sensor 1030, coupling detectors 1028, or tuning network 1010 along with a plastic or other housing can comprise a disposable tip 1032.

With reference again to FIGS. 3 and 4, an exemplary system 14 also includes display system 22 to provide images of the ROI 12 in certain exemplary embodiments wherein ultrasound energy is emitted from transducer 19 in a manner suitable for imaging. Display system can be any type of system that conveys images or information apart from images about system 14 or ROI 12 to the user. Therefore, display system 22 can be a computer monitor, television screen or it can be a simply type of indicator system such a liquid crystal display or light emitting diode display in various exemplary embodiments. Liquid crystal displays and light emitting diode displays are particularly useful when system 14 is a hand-held system.

Display system 22 enables the user to facilitate localization of the treatment area and surrounding structures, e.g., identification of a pilosebaceous unit 68 and sebaceous glands 70. After localization, delivery of ultrasound energy 72 at a depth, distribution, timing, and energy level to achieve the desired therapeutic effect to treat a sebaceous gland 70 is provided. Before, during, and/or after therapy, i.e., before, during and/or after delivery of ultrasound energy, monitoring of the treatment area and surrounding structures can be conducted to further plan and assess the results and/or providing feedback to control system 20 and a system operator via display system 22.

In accordance with an exemplary embodiment, localization can be facilitated through ultrasound imaging that can be used to define the position of a sebaceous gland 70 and/or the depth of sebaceous glands 70 in a ROI 12. Such glands can be seen lying along hair follicles and their image may be further enhanced via signal and image processing.

For ultrasound energy delivery, transducer 19 can be mechanically and/or electronically scanned to place treatment zones over an extended area in ROI 12. A treatment depth can be adjusted between a range of approximately 1 to 10 millimeters, and/or the greatest depth of sebaceous glands 70. Such delivery of energy can occur through imaging of the targeted sebaceous gland 70 and then applying ultrasound energy, or application of ultrasound energy at known depths over an extended area without initial or ongoing imaging.

With reference to FIG. 5A which depicts one exemplary embodiment, a treated zone 74 may extend over a line, plane, or surface, or over an extended zone across the sebaceous gland depth 76 that typically ranges from approximately 1 to 10 millimeters. Transducer 19 can be mechanically and/or electronically scanned, for example directionally along 78, to extend treatment zone 74 over a large area. Transducer 19 can be further scanned or moved along a longer directional line 80 to further enlarge treatment zone 74. For any treated zone 74, as treated zone 74 increases in depth within ROI 12, the cross sectional area of treated zone 74 may increase in size from small to medium to large.

The ultrasound beam from transducer 19 can be spatially and/or temporally controlled by changing the spatial parameters of transducer 19, such as the placement, distance, treatment depth and transducer 19 structure, as well as by changing the temporal parameters of transducer 19, such as the frequency, drive amplitude, and timing, with such control handled via control system 20. Such spatial and temporal parameters can also be suitably monitored and/or utilized in open-loop and/or closed-loop feedback systems within ultrasound system 16.

In accordance with another exemplary embodiment of the present invention, with reference to FIG. 5B, an exemplary monitoring method may comprise monitoring the temperature profile or other tissue parameters of ROI 12, such as attenuation, speed of sound, or mechanical properties such as stiffness and strain of the treatment region and suitably adjust the spatial and/or temporal characteristics and energy levels of ultrasound energy 72 emitted from transducer 19. The results of such monitoring techniques may be indicated on display system 22 by means of one-, two-, or three-dimensional images of monitoring results, or may simply comprise a success or fail-type indicator, or combinations thereof. Additional treatment monitoring techniques may be based on one or more of temperature, video, profilometry, and/or stiffness or strain gauges or any other suitable sensing technique.

In accordance with another exemplary embodiment, with continued reference to FIGS. 5A and 5B, system 14 can be configured for treatment over an expanded treatment ROI 12 that includes a combination of tissues, such as subcutaneous fat/adipose tissue 82 and muscle 84, among others. Multiple such tissues may be treated including sebaceous glands 70 in combination with at least one of epidermis 86, dermis 88, adipose tissue, muscular fascia lying atop muscle 84, mucous membrane, hair bulb, hair shaft, hair follicle between hair bulb and epidermis 86, blood vessels, apocrine sweat glands, eccrine glands lying within dermis 88, fat 82 or muscle 84, and/or any other tissue of interest.

In an exemplary embodiment, system 14 will emit energy under various temporal and/or spatial regimes to initiate at least one physiological effect within ROI 12. The physiological effects are the result of the increased temperature within ROI 12. Specifically, system 14 will emit energy within ROI 12 at specific depths between approximately 1-10 millimeters to target pilosebaceous units 68 and specifically sebaceous glands 70. In a particular exemplary embodiment, the heating occurs at a depth of approximately 1-5 millimeters to target pilosebaceous units 68.

While most pilosebaceous units 68 are located approximately 1-3 millimeters below the surface of skin 85, pilosebaceous units 68, particularly sebaceous glands 70 can swell which increases their depth below skin 85. In certain situations, the depth can be below 5 millimeters. Ultrasound energy 72 can still reach effectively target these inflamed sebaceous glands 70 at any depth below skin 85. In certain exemplary embodiments, the depth of these swollen sebaceous glands can be approximately 10 millimeters below the surface of skin 85.

Any amount of energy can be used during method 10 as long as the tissue within ROI 12 is not ablated or coagulated. In an exemplary embodiment, the energy emitted from probe 18 is unfocused or defocused ultrasound energy 72. Alternatively, focused ultrasound energy 72 could be emitted from probe 18 and applied to ROI 12.

In certain exemplary embodiments, system 14 is equipped with certain features to aid the user. One feature is a disposable tip that covers probe 18 during use. The disposable tip enables ultrasound energy 72 to pass through the tip and contact the patient. But, the disposable tip can be removed from probe 18 after use and replaced with a new disposable tip to prevent the spread of germs from one patient to another that might reside on probe 18 after contact with a patient's skin 85. Different size disposable tips can be used and fall within the scope of the present invention.

In one exemplary embodiment, the energy released into ROI 12 increases the local temperature within ROI 12 from approximately 1°-25° C. over a body's normal temperature. Therefore the temperature within ROI 12 during treatment is between approximately 35°-60° C. In another exemplary embodiment, the temperature is raised approximately 1°-15° C. over a body's normal temperature. Therefore, in this embodiment, the temperature within ROI 12 is between approximately 35°-49° C. While specific temperature ranges are disclosed herein, it should be noted that any temperature is considered to fall within the scope of the present invention.

In certain embodiments, the temperature increase may be very high but applied for a short enough time period so that the energy delivered to ROI 12 does not cause tissue ablation or coagulation. In other situations, the temperature increase may be fairly small and applied long enough to effect sebaceous glands 70 without causing tissue ablation or coagulation.

The time-temperature profile for method 10 can be modeled and optimized with the aid of the thermal dose concept. The thermal dose, or $t_{43}$, is the exposure time at 43° C. which causes an equivalent biological effect due to an arbitrary time-temperature heating profile. Typically an ablative lesion forms on the order of one second at 56° C., which corresponds to a thermal dose of one hundred and twenty minutes at 43° C. The same thermal dose corresponds to 50° C. for approximately one minute. Thus a non-ablative profile can contain high temperatures for very short times and/or lower temperatures for longer times or a combination of various time-temperature profiles. For example, temperatures as high as 56° C. for under one second or 46° C. for under fifteen minutes can be utilized. Such processes can be implemented in various exemplary embodiments, whereby one or more profiles may be combined into a single treatment.

In an exemplary embodiment the temperature at ROI 12 is raised to a high level, such as approximately 50° C. or more and held for several seconds. In another exemplary embodiment, the temperature is raised to a high level, (for example greater than 50° C.), for under one second up to five seconds or more, and then turned off for under one second up to five seconds or more, and repeated to create a pulsed profile.

In another exemplary embodiment, the temperature is raised quickly to a high level (greater than 50° C.), and then dropped to a lower temperature (less than 50° C.), and then maintained at that temperature for a given time period such as one second up to several seconds or over a minute.

In another exemplary embodiment, the temperature is increased quickly to a high level ($T_{HIGH}$), whereby $T_{HIGH}$ is greater than 40° C., and the power to system 14 is turned off, but turned on again once the temperature drops below a lower threshold, ($T_{LOW}$), whereby $T_{LOW}$ is less than $T_{HIGH}$. Once the temperature reaches $T_{HIGH}$ again power to system 14 is turned back off and this process is repeated, in effect acting like a thermostat. The process is terminated after a total treatment time of under one second to one minute or more.

In another exemplary embodiment, the temperature is raised quickly to a high level ($T_{START}$), whereby $T_{START}$ is greater than 40° C. and then turned off, but turned on again before the temperature drops appreciably (i.e. by a few degrees) below $T_{START}$, whereby the temperature may then increase a small amount (i.e. by a few degrees) over $T_{START}$ before the power is turned off again. In such an exemplary embodiment the temperature quickly reaches a starting point and then may be allowed to increase to a higher temperature yet still remain in a non-ablative or coagulative regime before the treatment is ended.

Figure 3:
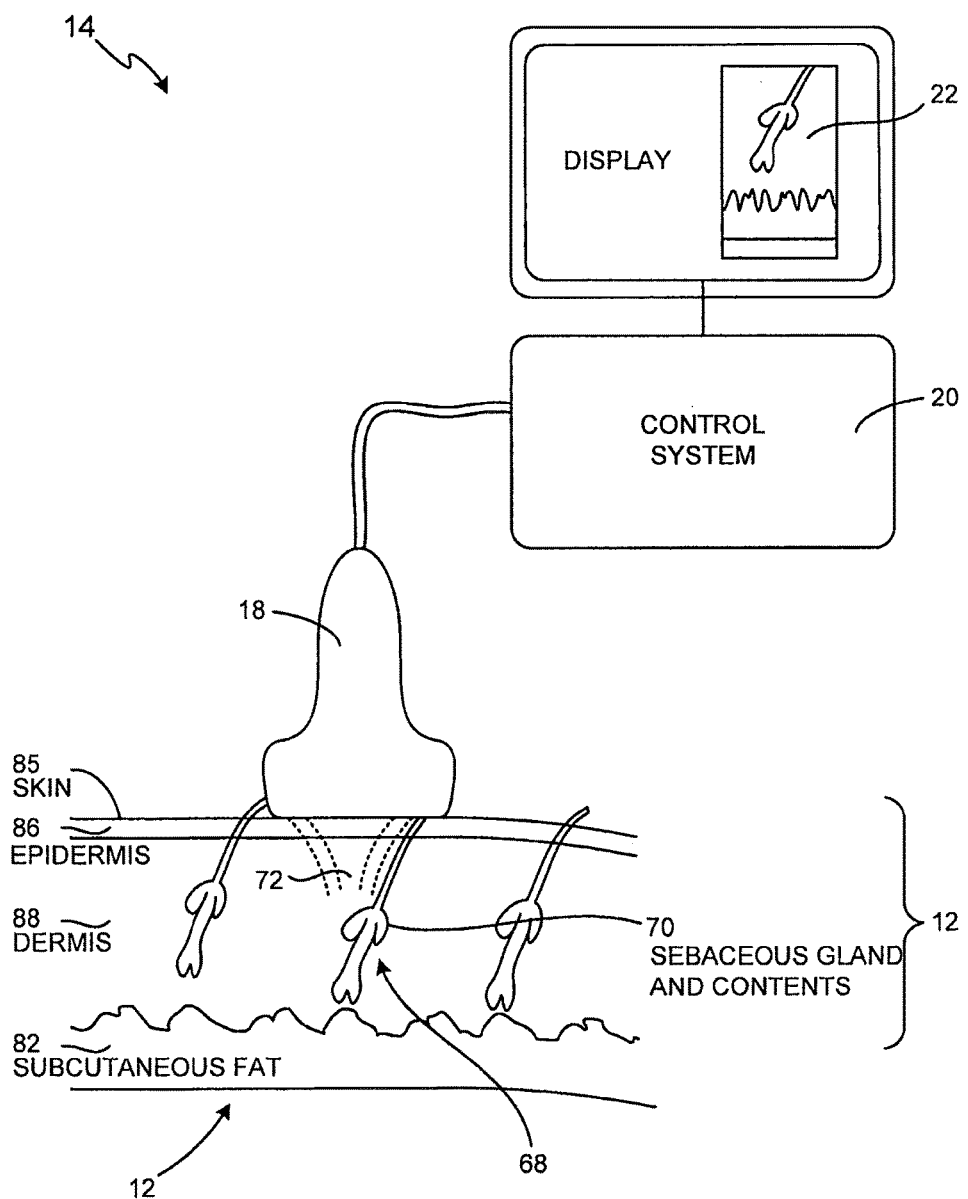
FIG. 3 illustrates a schematic diagram of a treatment system configured to treat a pilosebaceous unit in accordance with an exemplary embodiment of the present invention.

In accordance with another exemplary embodiment, an exemplary system 14 can also be configured to assist in drug delivery. In one exemplary embodiment, system 14 can be used for drug delivery as depicted in FIG. 3. In this embodiment, a medicinal agent 96 such as a cream is applied directly to the patient's skin 85 prior to the probe 18 being placed on skin 85. Medicinal agent 96 can contain medications or be otherwise useful in treating a patient. In an exemplary embodiment, medicinal agent 96 contains drugs used to treat acne or otherwise improve the condition of the patient's skin.

In an exemplary embodiment, medicinal agent 96 is also used to couple probe 18 to skin 85. Therefore, medicinal agent 96 can have multiple uses. First, medicinal agent 96 is used to couple probe 18 to skin 85. Second, since medicinal agent 96 contains drugs and other medicines, the medicines and drugs are delivered to the skin when energy is applied from probe 18. Finally, in an exemplary embodiment, the medicines and drugs within medicinal agent 96 are used for skin treatment. Therefore, as the patient is being treated by the application of energy at non-ablative levels, therapeutic drugs are also being administered to the patient to treat skin disorders such as acne.

The delivery of medicinal agent 96 can be enhanced by the application of ultrasound energy 72. Specifically, the heating at ROI 12 can cause better diffusion of medicinal agent 96 through the skin at ROI 12. Further, the mechanical effects of ultrasound energy 72 such as cavitation can also physically drive or push medicinal agent 96 through the skin and into ROI 12.

The application of ultrasound energy 72 to medicinal agent 96 can have certain advantages in the treatment of the patient. The efficacy of certain medicinal agents 96 can be increased by the application of ultrasound energy 72. Moreover, the efficiency of delivery of medicinal agent 96 can be increased by applying ultrasound energy 72 to medicinal agent 96. Further, certain medicinal agents 96 are inactive until they are exposed to energy or heat and the application of ultrasound energy 72 to medicinal agent 96 activates medicinal agent 96.

After medicinal agent 96 has been applied to skin 85, system 14 is used as normal and the increased heat below skin 85 within ROI 12 helps couple the drugs within medicinal agent 96 to the patient's body through known drug delivery techniques.

In addition to treating existing acne, method 10 can be used to prevent further acne from reoccurring at ROI 12. The same physiological effects described above that treat existing acne, also prevent new acne from occurring. Therefore, continuing to treat a patient with method 10 after existing acne has been treated new acne does not develop at ROI 12.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

What is claimed is:

1. A method for treating acne in a skin of a subject, the method comprising:
   a) identifying a sebaceous gland in a portion of the skin having the acne with ultrasound imaging; and
   b) delivering an ultrasound energy from a transducer probe to the sebaceous gland, the ultrasound energy configured to generate an elevated temperature in the sebaceous gland for a predetermined length of time, wherein the predetermined length of time allows a decrease of sebum and sebum production and does not allow ablation or coagulation of tissue within the sebaceous gland at the elevated temperature to treat existing acne and prevent future acne from developing.

2. The method according to claim 1, wherein the elevated temperature is in a range of 35° C. to 60° C.

3. The method according to claim 1, wherein the elevated temperature is greater than 50° C. and the predetermined length of time is greater than five seconds.

4. The method according to claim 1, wherein the elevated temperature and the predetermined length of time correspond to a thermal dose of less than one second at 56° C.

5. The method according to claim 1, wherein the sebaceous gland is located at a depth below a surface of the skin in a range of 1 millimeter to 10 millimeters and the ultrasound energy is delivered to the depth.

6. The method according to claim 1, wherein the ultrasound energy is focused ultrasound energy.

7. The method according to claim 6, the method further comprising moving a focal depth of the focused ultrasound energy to a different focal depth during the delivering the ultrasound energy of step b).

8. A method for treating acne in a skin of a subject, the method comprising:
   a) identifying a pilosebaceous tissue in a portion of the skin having the acne with ultrasound imaging, the pilosebaceous tissue containing at least one bacterium associated with the acne; and
   b) delivering an ultrasound energy from a transducer probe to the pilosebaceous tissue, the ultrasound energy configured to generate an elevated temperature in the pilosebaceous tissue for a predetermined length of time, wherein the predetermined length of time initiates programmed cell death in the at least one bacterium and does not allow ablation or coagulation of tissue within the pilosebaceous tissue at the elevated temperature to treat existing acne and prevent future acne from developing.

9. The method according to claim 8, wherein the elevated temperature is in a range of 35° C. to 60° C.

10. The method according to claim 8, wherein the elevated temperature is greater than 50° C. and the predetermined length of time is greater than five seconds.

11. The method according to claim 8, wherein the elevated temperature and the predetermined length of time correspond to a thermal dose of less than one second at 56° C.

12. The method according to claim 8, wherein the pilosebaceous tissue is located at a depth below a surface of the skin in a range of 1 millimeter to 10 millimeters and the ultrasound energy is delivered to the depth.

13. The method according to claim 8, wherein the ultrasound energy is focused ultrasound energy.

14. The method according to claim 13, the method further comprising moving a focal depth of the focused ultrasound energy to a different focal depth during the delivering the ultrasound energy of step b).

15. The method according to claim 8, wherein the at least one bacterium includes *Propionibacterium acnes*.

16. A method for treating acne in a skin of a subject, the method comprising:
   a) identifying a pilosebaceous tissue in a portion of the skin having the acne with ultrasound imaging;
   b) delivering an unfocused ultrasound energy from a transducer probe to the pilosebaceous tissue;
   c) sensing, using a sensor configured to sense an amount of ultrasound energy transferred to the pilosebaceous tissue, an amount of the unfocused ultrasound energy transferred to the pilosebaceous tissue; and
   d) in response to sensing that the amount of the unfocused ultrasound energy transferred to the pilosebaceous tissue has exceeded a predetermined threshold, stopping the delivering the unfocused ultrasound energy,
   wherein the predetermined threshold allows a physiological effect in the pilosebaceous tissue and does not allow ablation and coagulation of tissue within the pilosebaceous tissue to treat existing acne and prevent future acne from developing,
   wherein the physiological effect is selected from the group consisting of:
      increased blood perfusion;
      denaturing of proteins;
      inhibition of sebum production; and
      programmed cell death.

17. The method of claim 16, wherein the predetermined threshold corresponds to a temperature in the pilosebaceous tissue of greater than 50° C. for a length of time of more than five seconds.

18. The method of claim 16, wherein the predetermined threshold corresponds to a thermal dose of less than one second at 56° C.

19. The method of claim 16, wherein the unfocused ultrasound energy is defocused ultrasound energy.

20. The method of claim 16, the method further comprising:
   e) subsequent to step d), waiting a predetermined length of time to allow a temperature in the pilosebaceous tissue to lower; and
   f) repeating steps b), c), and d).

* * * * *

UNITED STATES PATENT AND TRADEMARK OFFICE
CERTIFICATE OF CORRECTION

PATENT NO. : 9,566,454 B2
APPLICATION NO. : 11/738682
DATED : February 14, 2017
INVENTOR(S) : Peter G. Barthe, Michael H. Slayton and Inder Raj S. Makin It is certified that error appears in the above-identified patent and that said Letters Patent is hereby corrected as shown below:

On the Title Page

Item (54) and in the Specification, Column 1, Line 1 in the Title - "SYSEM" should be -- SYSTEM --

In the Specification

Column 5, Line 63 - "P-acnes" should be -- P acnes --

Column 6, Line 22 - "P-acnes" should be -- P acnes --

Column 6, Line 23 - "P-acnes" should be -- P acnes --

Column 6, Line 44 - "P-acnes" should be -- P acnes --

Column 6, Line 57 - "P-acnes" should be -- P acnes --

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*